US010231980B2

(12) United States Patent
Gerloni

(10) Patent No.: US 10,231,980 B2
(45) Date of Patent: Mar. 19, 2019

(54) CORTEXOLONE 17ALPHA-BENZOATE FOR USE IN THE TREATMENT OF TUMOURS

(71) Applicant: COSMO TECHNOLOGIES LTD., Dublin (IE)

(72) Inventor: Mara Gerloni, San Diego, CA (US)

(73) Assignee: COSMO TECHNOLOGIES LTD., Dublin (IE)

( * ) Notice: Subject to any disclaimer, the term of this patent is extended or adjusted under 35 U.S.C. 154(b) by 0 days.

(21) Appl. No.: 15/517,659

(22) PCT Filed: Oct. 7, 2015

(86) PCT No.: PCT/EP2015/073176
§ 371 (c)(1),
(2) Date: Apr. 7, 2017

(87) PCT Pub. No.: WO2016/055537
PCT Pub. Date: Apr. 14, 2016

(65) Prior Publication Data
US 2017/0360806 A1 Dec. 21, 2017

(30) Foreign Application Priority Data
Oct. 8, 2014 (EP) ..................... 14188063

(51) Int. Cl.
*A61K 31/573* (2006.01)
*C07J 5/00* (2006.01)
*A61K 9/00* (2006.01)
*A61K 45/06* (2006.01)

(52) U.S. Cl.
CPC .......... *A61K 31/573* (2013.01); *A61K 9/0019* (2013.01); *A61K 9/0053* (2013.01); *A61K 45/06* (2013.01); *C07J 5/0053* (2013.01)

(58) Field of Classification Search
None
See application file for complete search history.

(56) References Cited

U.S. PATENT DOCUMENTS

| | | | |
|---|---|---|---|
| 3,152,154 A | 10/1964 | Ercoli et al. | |
| 3,530,038 A | 9/1970 | De Flines et al. | |
| 4,472,393 A | 9/1984 | Shapiro | |
| 5,990,099 A | 11/1999 | Clark | |
| 6,172,054 B1 | 1/2001 | Clark | |
| 7,186,753 B1 | 3/2007 | Del Soldato | |
| 7,687,484 B2 | 3/2010 | Bodor | |
| 8,785,427 B2 | 7/2014 | Mauro et al. | |
| 2009/0240049 A1 | 9/2009 | Villa et al. | |

FOREIGN PATENT DOCUMENTS

| | | |
|---|---|---|
| CN | 101397317 A | 4/2009 |
| DE | 4121484 A1 | 1/1993 |
| DE | 102006059063 A1 | 6/2007 |
| RU | 2506974 C1 | 2/2014 |
| WO | 8809337 A1 | 12/1988 |
| WO | 9009394 A2 | 8/1990 |
| WO | 0049993 A2 | 8/2000 |
| WO | 0240030 A1 | 5/2002 |
| WO | 03014141 A1 | 2/2003 |
| WO | 2007031349 A1 | 3/2007 |
| WO | 2007142842 A2 | 12/2007 |
| WO | 2009019138 A2 | 2/2009 |
| WO | 2009076170 A2 | 6/2009 |
| WO | 2011151252 A2 | 12/2011 |
| WO | 20120129305 A1 | 9/2012 |
| WO | 2016055533 A1 | 4/2016 |

OTHER PUBLICATIONS

Search Report and Written Opinion dated Dec. 17, 2015 in PCT/EP2015/073176 (14 pages).
Search Report dated Mar. 27, 2015 issued in counterpart European Patent Application No. 141880633.3 (11 pages).
G.Celasco et al. "Pharmacological Profile of 9,11-Dehydrocortexolone 17[alpha]-Butyrate (CB-03-04), a New Androgen Antagonist with Antigonadotropic Activity", Drug Research, Jan. 2005, pp. 581-587, vol. 55, No. 10.
P. Ferraboschi et al. "Lipase-catalyzed preparation of corticosteroid 17alpha-esters endowed with antiandrogenic activity", Tetrahedron Letters, Jul. 2008, pp. 4610-4612, vol. 49, No. 31.
T. Corbishley et al. "Androgen receptor in human normal and malignant pancreatic tissue and cell lines", Cancer, May 1986, pp. 1992-1995, vol. 57, No. 10.
Peterson, R. E.: "Biliary excretion of neutral steroids in man" Biliary System, Symp. Nato Advan. Study Inst., Newcastle-Upon-Tyne, England, 1963, 385, published in 1965, abstract only, retrieved from Accession No. 1966:87023, (2 pages).
J.J. Keating et al. "A prospective randomised controlled trial of tamoxifen and cyproterone acetate in pancreatic carcinoma", British Journal of Cancer, Nov. 1989, pp. 789-792, vol. 60, No. 5.
P. Ferraboschi et al."A full conformational characterization of antiandrogen cortexolone-17[alpha]-propionate and related compounds through theoretical calculations and nuclear magnetic resonance spectroscopy", MEDCHEMCOMM, Apr. 2014, pp. 904-914, vol. 5, No. 7.
Cutler, Gordon B., Jr. et al: "11-Deoxycortisol: a glucocorticoid antagonist in vivo", Endocrinology, 104: 1839, abstract only, retrieved from STN Database Accession No. 1979:469056, (2 pages).

(Continued)

*Primary Examiner* — Savitha M Rao
*Assistant Examiner* — Gregg Polansky
(74) *Attorney, Agent, or Firm* — Rothwell, Figg, Ernst & Manbeck, P.C.

(57) ABSTRACT

The present invention provides certain cortexolone derivatives of formula (I), and the same for use as antitumor active ingredients for the curative or adjuvant, or neoadjuvant or palliative treatment of precancerous lesions, dysplasias, metaplasias and tumor diseases, including malignant neoplasias and metastasis. Another aspect of the invention relates to pharmaceutical compositions comprising cortexolone derivatives of formula (I) as active ingredients and at least one physiologically acceptable excipient, and to the use of said pharmaceutical compositions as antitumor medicinal products.

14 Claims, 18 Drawing Sheets

(56) References Cited

OTHER PUBLICATIONS

S. Inagaki "17-alpha-Hydroxy Progesterone Caproate", J. Wakayam Med. Assoc., vol. 22, No. 3, May 1971, pp. 181-205.
R. M. Kelley et al. "The Role of Progesterone in Human Endometrial Cancer", Cancer Research, vol. 25, 1965, pp. 1190-1192.
A. Varga et al. "Effect of 17-alpha Hydroxyprogesterone 17-n-caproate on Various Pelvic Malignancies", Obstetrics and Gynecology, vol. 23, No. 1, Jan. 1964, pp. 51-62.
S. Patel et al. "Effect of 17-alpha hydroxyprogesterone caproate on the production of tumor necrosis factor-alpha and the expression of cyclooxygenase-2 in lipopolysaccharide-treated gravid human myometrial explants", Journal of Perinatalogy, 2010, vol. 30, pp. 584-589.
G. Celasco et al. "Biological Profile of Cortexolone 17-alpha-Propionate (CB-03-01), a New Topical and Peripherally Selective Androgen Antagonist", Arzneim-Forsch/Drug Research, vol. 54, No. 12, 2004, pp. 881-886.

(a) Prostate Cancer Cell Viability (b) Pancreatic Cancer Cell Viability

CORTEXOLONE 17ALPHA-BENZOATE FOR USE IN THE TREATMENT OF TUMOURS

CROSS-REFERENCE TO RELATED APPLICATIONS

The present application is a national stage filing under 35 U.S.C. § 371 of PCT/EP2015/073176, filed on 7 Oct. 2015, and claims the benefit of priority to European Patent Application No. 14188063.3, filed 8 Oct. 2014. Each application is incorporated herein by reference in its entirety.

RELATED APPLICATIONS

The instant application claims the benefit of priority under 35 USC $ 119 to European Patent Application No. 14188063.3, entitled "17α-monoesters and 17α, 21-diesters of cortexolone for use in the treatment of tumors" filed 8 Oct. 2014 the entire contents of which are incorporated herein by reference in their entirety.

In a general context, the present invention provides certain cortexolone derivatives of formula (I)

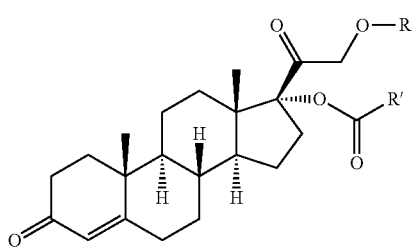

and the same for use as antitumor active ingredients for the curative or adjuvant, or neoadjuvant or palliative treatment of precancerous lesions, dysplasias, metaplasias and tumor diseases, including malignant neoplasias and metastasis.

Another aspect of the invention relates to pharmaceutical compositions comprising at least one cortexolone derivative of formula (I) as active ingredient with at least one physiologically acceptable excipient, and to the same pharmaceutical compositions for use as antitumor medicinal products for the curative or adjuvant, or neoadjuvant or palliative treatment of precancerous lesions, dysplasias, metaplasias and tumor diseases, including malignant neoplasias and metastasis.

BACKGROUND OF THE INVENTION

Tumor, or neoplasm, is defined as a mass of new tissue which persists and grows independently of its surrounding structures, and which has no physiological use (Doreland's Medical Dictionary, 23 ED. 1960).

Several classifications are available for tumors: for the exploitation of this patent application, the most important are the epithelial tumors.

The epithelial tumors are neoplasms derived from epithelial cells, the type of cell which lines hollow internal organs and body surfaces; this group includes many of the most common cancers, and includes most of those developing in the breast, prostate, lung, pancreas, and gastrointestinal tract.

In some cases, the epithelial tumors can also be characterized by the presence of specific hormone-receptors in the tumor cells which gives to the tumor an hormone-sensitivity.

Carcinomas, that are malignant tumors derived from epithelial cells, make up about 85 out of every 100 cancers (85%).

One example of epithelial carcinoma is the pancreatic carcinoma (also referred to as pancreatic cancer).

Pancreatic cancer is one of the most deadly forms of carcinomas. The exocrine and endocrine cells of the pancreas form completely different types of tumors. Exocrine pancreatic tumors constitute the most common type of pancreatic cancer (more than 95%). Although benign (non-cancerous) cysts and benign tumors (adenomas) may develop in the pancreas, most of the exocrine pancreatic tumors are malignant.

The carcinoma of pancreas, particularly exocrine pancreas carcinoma and much more particularly the most frequent one, that is ductal adenocarcinoma, falls into the five most frequent causes of death in males, and is the fourth cause of death in females. It is one of the tumors with the highest unfavorable prognosis, with a survival of only 5% in males and 6% in the females at 5 years after diagnosis. The highest incidence occurs between 60-70 years of age (AIOM. Linea Guida Carcinoma del Pancreas Esocrino, ed. 2013).

The etiology of the exocrine pancreas carcinoma is unknown. There is a recognized genetic predisposition (familiarity) and some risk factors such as smoke, fatty diet, diabetes mellitus type 2, chronic pancreatitis, environmental factors such as solvents or pesticides.

The carcinoma of the exocrine pancreas is, in its early stage, asymptomatic, and this explains the delay in the diagnosis, which is usually performed when the disease is at an advanced stage, with exception for accidental detection during diagnostic procedures for other abdominal diseases.

Patients diagnosed with pancreatic cancer typically have a poor prognosis: considering the above described delay in the diagnosis, only about 15% of cases show the tumor limited to the pancreas, whereas in the remaining cases, the diffusion to the loco-regional lymph nodes is detected in about 25% of the patients, and the presence of metastases is detected in 60% of the cases.

Median survival from diagnosis of the cancer is approximately three to six months, while a five-year survival is significantly less than 5%.

The therapy of carcinoma of the pancreas is surgery, when possible, also with palliative purposes.

Radical pancreaticoduodenectomy is currently the only chance of cure, especially for minimal disease.

The medical therapy, also associated to radiotherapy, is limited to the unresectable cases, or when metastases are present, or as adjuvant treatment after surgery. Although there are occasional reports of individual patients who respond to gemcitabine or fluorouracil, or combination regimens with doxorubicin, methotrexate, cisplatin, oxaliplatin, irinotecan, erlotinib and so on, the results of chemotherapy are generally unsatisfactory and often no better than no treatment at all (Martindale, 31 ed., page 530).

Theve et al in 1983 reviewed possible effects of sex hormones on the pancreas, based on reports on steroid receptor proteins in pancreatic tissue, the high capacity of estrogen binding protein in the human pancreas and capacity of human pancreatic tissue to convert the main peripheral estrogen, estrone sulphate, into the terminal biologically active estradiol-17 beta.

With this background, they tried tamoxifen (an antagonist of the estrogen receptor) in patients with unresectable adenocarcinoma of the pancreas with some preliminary results similar to those by Wong et al. in 1993.

The clinical practice in the subsequent years did not give the expected results, but the conclusion was that even if anti-estrogens did not constitute the optimal form of therapy, other sorts of hormonal manipulation ought to be tried in pancreatic cancer. In view of the above, there is a strong need for new approaches of tumor treatment and, in particular, for the treatment of carcinomas, and still more especially for the treatment of epithelial tumors, especially prostatic carcinoma or pancreas carcinoma (preferably exocrine pancreas carcinoma).

A number of compounds referred to as 17α-monoesters, 21-monoesters and 17α,21-diesters of cortexolone and processes for their manufacturing are known in the art. WO03/014141 describes compounds belonging to the family of steroids structurally related to cortexolone (also known as 11-deoxycortisone) as having mainly antiandrogenic activity. These compounds, such as cortexolone 17α-propionate, act by interfering with the direct action of the androgenic hormones on the androgen receptor (AR) in the tissues.

WO2007/031349 discloses $C_3$-$C_{10}$ 17α-esters of 9,11-dehydrocortexolone, a derivative structurally related to cortexolone, as antigonadotrophic agents, which may be useful for the treatment disorders closely related to excess of gonadotrophin production.

WO2009/019138 discloses an enzymatic process for the obtainment of 17α-monoesters of cortexolone and of 9,11-dehydrocortexolone; furthermore, it also discloses the existence of several crystalline forms of cortexolone 17α-propionate, namely crystalline form I, form II, form III and hydrate form IV, and certain processes to obtain them.

Cyproterone Acetate (abbreviated as CPA), is a synthetic steroid, which is considered as the standard therapy for the treatment of androgen-sensitive tumors, especially prostate cancer. The standard therapy with Cyproterone Acetate resulted quite ineffective in the tumors with reduced, or absent, expression of androgen receptor (Br. J. Cancer (1989), 60, 789-792).

It is known in the art that the presence of 17α-esterification confers to cortexolone 17α-esters different antiandrogenic activities, demonstrated in animals (Celasco et al. Arzneim-Forsch 2005; 5: 581-7).

It has now been surprisingly found that cortexolone 17α(alpha)-monoesters, 21-monoesters and 17α(alpha),21-diesters have unexpected antitumor effects, both in isolated cancer cell and in xenograft prostate and pancreatic carcinomas into the animals.

The antitumor effect of the invention was evident both in carcinoma cells harboring androgen receptor ($AR^+$), such as in the case of prostate cancer cells LNCaP or pancreatic cancer cells Panc1, and, very surprisingly, also in cells with absent, or reduced, expression of the androgen receptor ($AR^-$), as prostate cancer cells PC3, or pancreatic cancer cells MiaPaca. The antitumor effect of the invention was also evident in mammary carcinomas and GI tract carcinomas.

BRIEF DESCRIPTION OF THE FIGURES

The invention will now be described by the following non-limiting figures and examples.

DEFINITIONS

Figure 1:
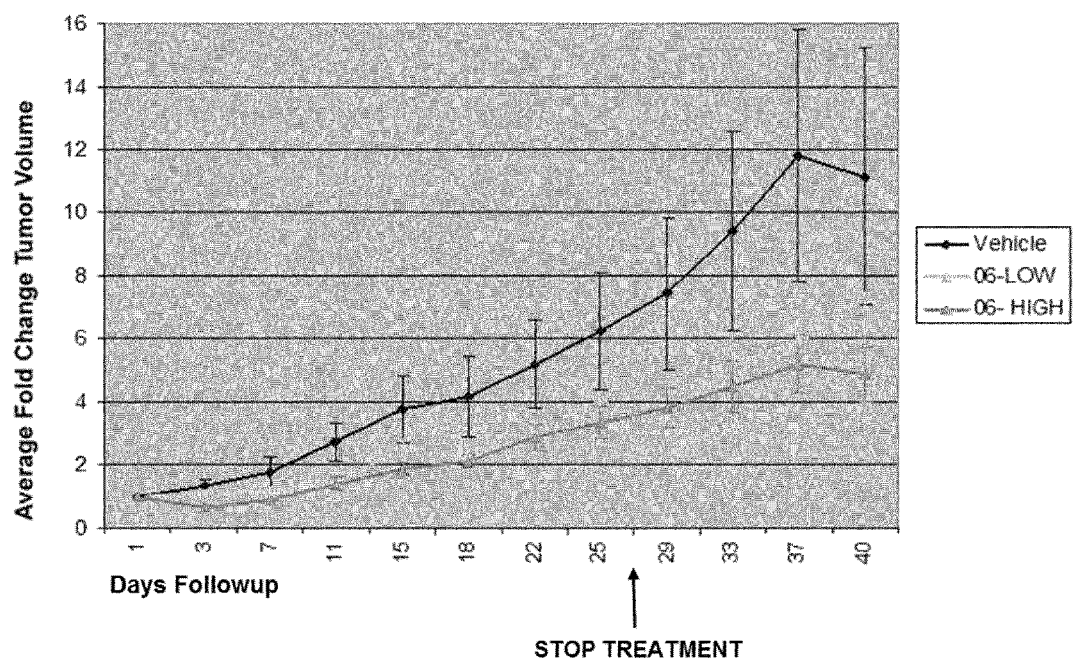
FIG. 1: Average change in pancreatic tumor volume, measured relatively to the start of treatment, in the xenograft animal model of nude mice (MiaPaca pancreatic cell line) with cortexolone 17α-benzoate (in the figure referred to as "06" and as "CB-03-06") at low dose (230 μM) and at high dose (1150 μM). Reference to "Vehicle" is a control treated group with 0.4% (v/v) tween 80 and 0.5% (w/v) carboxymethylcellulose in normal saline. Mice were treated with the compound and vehicle SC daily for 28 consecutive days. The stop treatment arrow refers to the day when the treatment was ended.

Unless otherwise defined, all terms of art, notations and other scientific terminology used herein are intended to have the meanings commonly understood by those skilled in the art to which this disclosure pertains. In some cases, terms with commonly understood meanings are defined herein for clarity and/or for ready reference; thus, the inclusion of such definitions herein should not be construed to represent a substantial difference over what is generally understood in the art.

In particular, the terms "physiologically acceptable excipient" or "pharmaceutically acceptable excipient" herein refer to a substance devoid of any pharmacological effect of its own and which does not produce adverse reactions when administered to a mammal, preferably a human. Physiologically acceptable excipients are well known in the art and are disclosed, for instance in the Handbook of Pharmaceutical Excipients, sixth edition (2009), herein incorporated by reference.

The term "alkyl" as used herein means a saturated straight or branched chain hydrocarbon.

The term "aryl" herein refers to aromatic mono- and poly-carbocyclic ring systems, wherein the individual carbocyclic rings in the poly-carbocyclic ring systems may be fused or attached to each other via a single bond. Suitable "aryl" groups comprise, but are not limited to, phenyl, naphthyl, biphenyl, and the like.

The term "heteroaryl" herein refers to an aromatic mono- and poly-carbocyclic ring system comprising at least a heteroatom in the ring system, wherein said heteroatom is selected in the group comprising, but not limited to, nitrogen, sulphur, oxygen and the like, and wherein the individual cyclic rings in the poly-carbocyclic ring systems may be fused or attached to each other via a single bond. Suitable "heteroaryl" groups comprise, but are not limited to, pyridyl, imidazolyl, pyrrolyl, furyl, benzimidazolyl, thiofuranyl and the like.

"Aryl group" may optionally substituted in at least one of the carbon atoms of the ring with a group selected from lower alkyl, lower alkenyl, lower halo alkyl, lower haloalkenyl, lower alkoxy, lower halcalkenyl, lower alkenyloxy, halogen, nitro, cyano, lower alkylthio, and the like.

"Heteroaryl group" may optionally be substituted in at least one of the carbon atoms or in at least one of the heteroatoms of the ring with a group selected from lower alkyl, lower haloalkyl, lower alkoxy, lower alkenyl, lower halcalkenyl, lower alkenyloxy, halogen, nitro, cyano, lower alkylthio, and the like.

The term "approximately" herein refers to the range of the experimental error, which may occur in a measurement.

The terms "comprising", "having", "including" and "containing" are to be construed as open-ended terms (i.e. meaning "including, but not limited to") and are to be considered as including and/or providing support also for terms as "consist essentially of", "consisting essentially of", "consist of" or "consisting of".

The terms "consist essentially of", "consisting essentially of" are to be construed as a semi-closed terms, meaning that no other ingredients which materially affects the basic and novel characteristics of the invention are included (optional excipients may thus be included).

The terms "consists of", "consisting of" are to be construed as a closed term.

As used herein, the terms "therapeutically effective amount" and "effective amount" refer to an amount sufficient to elicit the desired biological response. In the present invention the desired biological response is to inhibit, reduce or ameliorate the severity, duration, progression, or onset of a disease, disorder or condition, prevent the advancement, recurrence, or progression of a disease, disorder or condition or a symptom associated with a disease, disorder or condition. The precise amount of compound administered to a subject will depend on the mode of administration, the type and severity of the disease, disorder or condition and on the characteristics of the subject, such as general health, age, sex, body weight and tolerance to drugs. The skilled artisan will be able to determine appropriate dosages depending on these and other factors. Suitable dosages are known for approved agents and can be adjusted by the skilled artisan according to the condition of the subject, the type of condition(s) being treated and the amount of a compound described herein being used. In cases where no amount is expressly noted, an effective amount should be assumed. For example, compounds and pharmaceutical compositions described herein can be administered to a subject in a dosage range from between approximately 0.01 to 100 mg/kg body weight/day for therapeutic treatment.

As used herein, the terms "treat", "treatment" and "treating" refer to therapeutic treatments includes the reduction or amelioration of the progression, severity and/or duration of a disease, disorder or condition, or the amelioration of one or more symptoms (specifically, one or more discernible symptoms) of a disease, disorder or condition, resulting from the administration of one or more therapies (e.g., one or more therapeutic agents such as a compound or composition of the invention). In specific embodiments, the therapeutic treatment includes the amelioration of at least one measurable physical parameter of a disease, disorder or condition. In other embodiments the therapeutic treatment includes the inhibition of the progression of a condition, either physically by, e.g., stabilization of a discernible symptom, physiologically by, e.g., stabilization of a physical parameter, or both. In other embodiments the therapeutic treatment includes the reduction or stabilization of a disease, disorder or condition.

The term "curative treatment" as used herein refers to a treatment that aims to cure a disease or to improve symptoms associated with a disease.

The term "palliative treatment" as used herein refers to a treatment or therapy that does not aim at curing a disease but rather at providing relief.

The term "adjuvant treatment" as used herein refers to a treatment that is given in addition to the primary, main or initial treatment.

The term "neoadjuvant treatment" as used herein refers to a treatment that is given before a main treatment, with the aim of reducing the size or extent of a tumor, thus reducing the consequences of a more extensive treatment technique that would be required if the tumor wasn't reduced in size or extent.

As described herein, compounds of the invention may optionally be substituted with one or more substituents, such as illustrated generally below, or as exemplified by particular species of the invention. It will be appreciated that the phrase "optionally substituted" is used interchangeably with the phrase "substituted or unsubstituted." In general, the term "substituted", whether preceded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position. When the term "optionally substituted" precedes a list, said term refers to all of the subsequent substitutable groups in that list. If a substituent radical or structure is not identified or defined as "optionally substituted", the substituent radical or structure is unsubstituted.

Selection of substituents and combinations of substituents envisioned by this invention are those that result in the formation of stable or chemically feasible compounds. The term "stable", as used herein, refers to compounds that are not substantially altered when subjected to conditions to allow for their production, detection, and, specifically, their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week. Only those choices and combinations of substituents that result in a stable structure are contemplated. Such choices and combinations will be apparent to those of ordinary skill in the art and may be determined without undue experimentation.

The term "simultaneous, separate or sequential administration" herein refers to administration of the first and second compound at the same time or in such a manner that the two compounds act in the patient's body at the same time or administration of one compound after the other compound in such a manner to provide a therapeutic effect. In some embodiments the compounds are taken with a meal. In other embodiments, the compounds are taken after a meal, such as 30 minutes or 60 minutes after a meal. In some embodiments, one compound is administered to a patient for a time period followed by administration of the other compound.

As used herein, the terms "subject" and "patient" are used interchangeably. The terms "subject" and "patient" refer to an animal (e.g., a bird such as a chicken, quail or turkey, or a mammal), specifically a "mammal" including a non-primate (e.g., a cow, pig, horse, sheep, rabbit, guinea pig, rat, cat, dog, and mouse) and a primate (e.g., a monkey, chimpanzee and a human), and more specifically a human. In one embodiment, the subject is a human.

DETAILED DESCRIPTION OF THE INVENTION

Now it has been surprisingly discovered that some cortexolone derivatives have therapeutically interesting anti-tumoral properties, against tumors, preferably epithelial and/or hormone-dependent tumors.

According to the general concept, the present invention is represented by the compounds of formula I

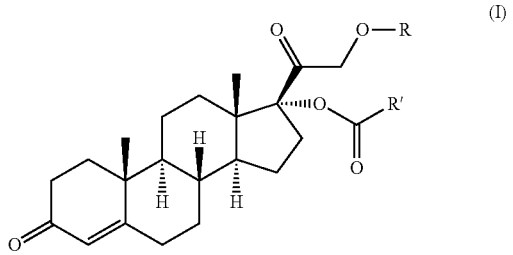

wherein R is hydrogen or C(O)—R₁, wherein R₁ is a linear alkyl chain containing 2 to 5 carbon atoms, and wherein R' is a linear alkyl chain containing 3 to 6 carbon atoms or an optionally substituted aryl group or an optionally substituted heteroaryl group. Preferred compounds of formula (I) are those wherein R is hydrogen or C(O)—R₁, wherein R₁CH₂CH₃ and wherein R' is —(CH₂)₃—CH₃ or phenyl.

The most preferred compound of formula (I) is the compound wherein R is hydrogen and R' is phenyl, that is cortexolone 17α-benzoate (herein also referred to as "06" or as "CB-03-06"), whose formulas are reported herein below.

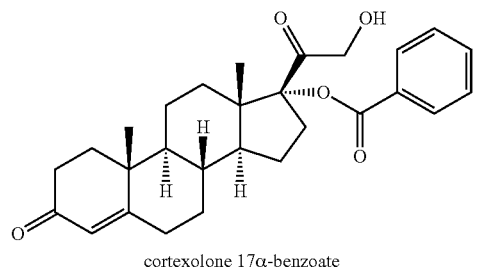

cortexolone 17α-benzoate

Pharmaceutically Acceptable Salts, Solvates, Chlatrates, Prodrugs and Other Derivatives The compounds described herein can exist in free form, or, where appropriate, as salts. Those salts that are pharmaceutically acceptable are of particular interest since they are useful in administering the compounds described below for medical purposes. Salts that are not pharmaceutically acceptable are useful in manufacturing processes, for isolation and purification purposes, and in some instances, for use in separating stereoisomeric forms of the compounds of the invention or intermediates thereof.

As used herein, the term "pharmaceutically acceptable salt" refers to salts of a compound which are, within the scope of sound medical judgment, suitable for use in contact with the tissues of humans and lower animals without undue side effects, such as, toxicity, irritation, allergic response and the like, and are commensurate with a reasonable benefit/risk ratio.

Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds described herein include those derived from suitable inorganic and organic acids and bases. These salts can be prepared in situ during the final isolation and purification of the compounds.

It should be understood that this invention includes mixtures/combinations of different pharmaceutically acceptable salts and also mixtures/combinations of compounds in free form and pharmaceutically acceptable salts.

In addition to the compounds described herein, pharmaceutically acceptable solvates (e.g., hydrates) and clathrates of these compounds may also be employed in compositions to treat or prevent the herein identified disorders.

As used herein, the term "pharmaceutically acceptable solvate," is a solvate formed from the association of one or more pharmaceutically acceptable solvent molecules to one of the compounds described herein. The term solvate includes hydrates (e.g., hemihydrate, monohydrate, dihydrate, trihydrate, tetrahydrate, and the like).

As used herein, the term "hydrate" means a compound described herein or a salt thereof that further includes a stoichiometric or non-stoichiometric amount of water bound by non-covalent intermolecular forces.

As used herein, the term "clathrate" means a compound described herein or a salt thereof in the form of a crystal lattice that contains spaces (e.g., channels) that have a guest molecule (e.g., a solvent or water) trapped within.

In addition to the compounds described herein, pharmaceutically acceptable derivatives or prodrugs of these compounds may also be employed in compositions to treat or prevent the herein identified disorders.

A "pharmaceutically acceptable derivative or prodrug" includes any pharmaceutically acceptable ester, salt of an ester or other derivative or salt thereof of a compound described herein which, upon administration to a recipient, is capable of providing, either directly or indirectly, a compound described herein or an inhibitory active metabolite or residue thereof. Particularly favored derivatives or prodrugs are those that increase the bioavailability of the compounds when such compounds are administered to a patient (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds described herein include, without limitation, esters, amino acid esters, phosphate esters, metal salts and sulfonate esters.

Medical Uses

In a general context, the present invention is represented by the compounds of formula (I) for use as a medicament.

For example, the invention relates to said compounds of formula (I) for use as a glucocorticoid receptor (GR) modulator, preferably a glucocorticoid antagonist.

In yet another aspect, the invention relates to said compounds of formula (I) for use of treating a disease or disorder mediated by glucocorticoid.

In still another aspect, the invention relates to said compounds of formula (I) for use in the treatment of precancerous lesions, dysplasias, metaplasias and tumor diseases, including malignant neoplasias and metastasis; according to another aspect, such a treatment may be curative, adjuvant, neoadjuvant or palliative.

Ideally, the invention relates to said compounds of formula (I) for use as an anti-tumor agent.

An object of the present invention is represented by cortexolone 17α-benzoate (CB-03-06) for use as a medicament.

In another aspect, the invention relates to cortexolone 17α-benzoate for use as a glucocorticoid receptor modulator, preferably a glucocorticoid antagonist.

In yet another aspect, the invention relates to cortexolone 17α-benzoate for use in treating a disease or disorder mediated by glucocorticoid.

In still another aspect, the invention relates to cortexolone 17α-benzoate for use in the treatment of precancerous lesions, dysplasias, metaplasias and tumor diseases, including malignant neoplasias and metastasis; according to another aspect, such a treatment may be curative, adjuvant, neoadjuvant or palliative.

Ideally, cortexolone 17α-benzoate is for use as an anti-tumor agent.

In an embodiment, said tumor diseases are solid tumors, preferably epithelial tumors, such as, by way of example, prostate carcinoma, mammary carcinoma, pancreatic carcinoma, lung carcinoma, gastrointestinal tract carcinoma (preferably colon carcinoma), kidney cancer, thyroid carcinoma, uterine carcinoma and adrenal carcinoma and the like.

In a preferred embodiment of the invention herein disclosed, said epithelial tumors are prostate carcinoma, pancreatic cancer (preferably exocrine pancreatic carcinoma), gastrointestinal tract carcinoma (preferably colon carcinoma) and mammary carcinoma (preferably triple negative breast cancer (TNBC)).

In a preferred embodiment of the invention herein disclosed, the tumor diseases are prostate cancer. In a preferred embodiment of the invention herein disclosed, the prostate cancer is an adenocarcinoma. In a preferred embodiment of the invention herein disclosed, the tumor diseases are prostate cancer with absent or reduced expression of the androgen receptor. In another preferred embodiment of the invention, the tumor diseases are prostate cancer with mutated or truncated Androgen Receptors.

Ideally, Cortexolone 17α-benzoate (CB-03-06) is for use as an anti-tumor agent where the tumor diseases are prostate cancer with mutated or truncated Androgen Receptors. One particularly advantageous use of Cortexolone 17α-benzoate (CB-03-06), is for use in the treatment of prostate cancers that are or have become resistant to anti-androgen treatment, such as enzalutamide. This is a particularly advantageous embodiment of the invention as it has recently been found that after 6 months of treatment 30% of cancers became resistant to enzalutamide because the AR has mutated or changed. Interestingly these resistant cancer cells upregulate the GR. Cortexolone 17α-benzoate (CB-03-06), can treat such cancers as the activity is also mediated through the GR.

In another preferred embodiment of the invention herein disclosed, the exocrine pancreatic carcinoma is an adenocarcinoma. In a preferred embodiment the exocrine pancreatic cancer with absent or reduced expression of the androgen receptor.

In a preferred embodiment of the invention herein disclosed, said epithelial tumors is gastrointestinal tract carcinoma (preferably colon carcinoma).

In a still preferred embodiment of the invention herein disclosed, said epithelial tumors is mammary carcinoma (preferably triple negative breast cancer). Optionally, the subject or patient being treated is a non-responder or relapse to conventional therapy.

In a preferred embodiment, the present invention provides the compound of formula (I) wherein R is hydrogen and R' is phenyl, that is cortexolone 17α-benzoate (herein also referred to as "06" or as "CB-03-06"), for use in the treatment of precancerous lesions, dysplasias, metaplasias and tumor diseases, including malignant neoplasias and metastasis; according to another aspect, such a treatment may be curative, adjuvant, neoadjuvant or palliative. Another object of the present invention is cortexolone 17α-valerate (herein also referred to as "05" or as "CB-03-05"), represented by:

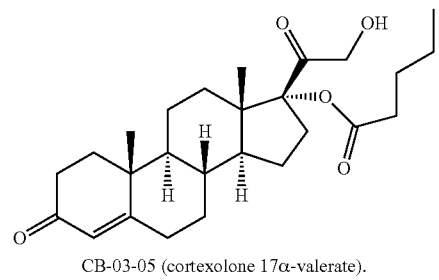

CB-03-05 (cortexolone 17α-valerate).

for use as a medicament. CB-03-05 (cortexolone 17α-valerate) will be discussed below and can be used as a medicament to treat the same conditions as described above in relation to cortexolone 17α-benzoate (CB-03-06).

Another object of the present invention is compounds of formula I, preferably cortexolone 17α-benzoate or cortexolone 17α-valerate, or pharmaceutical formulations comprising said compounds, for use in the manufacture of medicament. For example, the compounds of formula I, preferably cortexolone 17α-benzoate or cortexolone 17α-valerate, or pharmaceutical formulations comprising said compounds may be for use in the manufacture of medicament for the treatment of precancerous lesions, dysplasias, metaplasias and tumor diseases, including malignant neoplasias and metastasis; according to another aspect, such a treatment may be curative, adjuvant, neoadjuvant or palliative. Ideally, these compounds or pharmaceutical formulations comprising said compounds are for use in the manufacture of an anti-tumor agent, In an embodiment, said tumor diseases are solid tumors, preferably epithelial tumors, such as, by way of example, prostate carcinoma, mammary carcinoma (preferably triple negative breast cancer), pancreatic carcinoma (preferably exocrine pancreatic carcinoma), lung carcinoma, gastrointestinal tract carcinoma (preferably colon carcinoma), kidney cancer, thyroid carcinoma, uterine carcinoma and adrenal carcinoma and the like.

In another aspect, the invention relates to compounds of formula I, cortexolone 17α-benzoate or cortexolone 17α-valerate, or pharmaceutical formulations comprising said compounds, for use in the manufacture of a medicament for treating a disease or disorder mediated by glucocorticoid.

In one aspect, the invention herein disclosed provides a method for treating precancerous lesions, dysplasias, metaplasias and tumor diseases, including malignant neoplasias and metastasis, said method comprising the administration of an effective amount of a compound of formula (I) to a subject in need thereof:

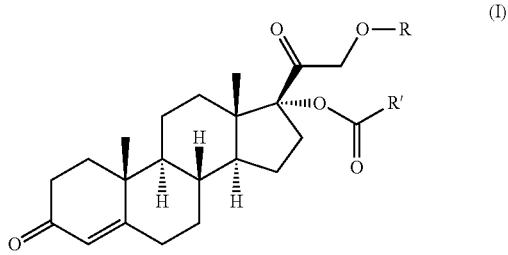

wherein R is hydrogen or C(O)—$R_1$, wherein $R_1$ is a linear alkyl chain containing 2 to 5 carbon atoms, and wherein R' is a linear alkyl chain containing 3 to 6 carbon atoms or an optionally substituted aryl group or an optionally substituted heteroaryl group, to a mammal in need thereof. Preferably, said mammal is a human.

Preferably, the invention herein disclosed provides a method for treating precancerous lesions, dysplasias, metaplasias and tumor diseases, including malignant neoplasias and metastasis, said method comprising the administration of an effective amount of a cortexolone 17α-benzoate or cortexolone 17α-valerate to a mammal in need thereof. Preferably, said mammal is a human.

In a preferred embodiment, the invention herein disclosed provides a method for treating tumors, said method comprising the administration of an effective amount of a cortexolone 17α-benzoate or cortexolone 17α-valerate to a mammal in need thereof. In these embodiments, said tumor diseases are solid tumors, particularly epithelial tumors, such as, by way of example, prostate carcinoma, mammary carcinoma (preferably triple negative breast cancer), uterine carcinoma, pancreatic carcinoma (preferably exocrine pancreatic carcinoma), lung carcinoma, gastro-intestinal tract carcinoma (preferably colon carcinoma), kidney cancer, thyroid carcinoma, uterine carcinoma and adrenal carcinoma and the like.

In a preferred embodiment of the invention herein disclosed, said epithelial tumors are prostate carcinoma, pancreatic carcinoma, more preferably exocrine pancreatic carcinoma, or mammary carcinoma, such as, triple negative breast cancer. Optionally, the subject or patient being treated is a non-responder or relapse to conventional therapy.

In a most preferred embodiment, said method comprises the administration of an effective amount of a compound of formula (I) wherein R is hydrogen and R' is phenyl, that is cortexolone 17α-benzoate.

The compounds of the present invention can be used in different therapeutic applications, especially oncologic applications.

The compounds according to the invention herein disclosed have been found particularly effective for the curative or adjuvant, or neoadjuvant or palliative treatment of pancreatic carcinoma, preferably exocrine pancreatic carcinoma, and prostatic carcinoma.

An illustration of the pharmacological properties of the compounds of the invention will be found hereafter in the experimental section.

The compounds of formula (I) may be prepared according to any conventional method, for instance by the processes disclosed in WO03/014141 and in WO2009/019138, the contents of which are herein incorporated by reference in their entirely. According to an embodiment of the invention, these compounds can be prepared according to the method disclosed in examples 10 and 11, respectively.

Pharmaceutical Compositions

The compounds described herein can be formulated into pharmaceutical compositions that further comprise a pharmaceutically acceptable carrier, diluent, adjuvant or vehicle. In one embodiment, the present invention relates to a pharmaceutical composition comprising a compound of the invention described herein, and a pharmaceutically acceptable carrier, diluent, adjuvant or vehicle. In one embodiment, the present invention is a pharmaceutical composition comprising an effective amount of a compound of the present invention or a pharmaceutically acceptable salt thereof and a pharmaceutically acceptable carrier, diluent, adjuvant or vehicle. Pharmaceutically acceptable carriers include, for example, pharmaceutical diluents, excipients or carriers suitably selected with respect to the intended form of administration, and consistent with conventional pharmaceutical practices.

According to a most preferred embodiment, said pharmaceutical composition comprises, as active ingredient, cortexolone 17α-benzoate (CB-03-06), in association with at least one physiologically acceptable excipient.

According to another preferred embodiment, said pharmaceutical composition comprises, as active ingredient, cortexolone 17α-valerate (CB-03-05), in association with at least one physiologically acceptable excipient.

In a further object, said pharmaceutical composition is for use as a medicament. In a further object, said pharmaceutical composition is for use in the treatment of precancerous lesions, dysplasias, metaplasias and tumor diseases, including malignant neoplasias and metastasis; according to another aspect, such a treatment may be curative, adjuvant, neoadjuvant or palliative.

In a further object, said pharmaceutical composition is for as an anti-tumor agent.

Preferably, said tumor diseases are solid tumors. More preferably, said solid tumors are epithelial tumors, such as, by way of example, prostate carcinoma, mammary carcinoma, pancreatic carcinoma, lung carcinoma, gastro-intestinal tract carcinoma (preferably colon carcinoma), kidney cancer, thyroid carcinoma, uterine carcinoma and adrenal carcinoma and the like.

In a preferred embodiment of the invention herein disclosed, said epithelial tumors are prostate carcinoma and pancreatic carcinoma, more preferably exocrine pancreatic carcinoma, gastrointestinal tract carcinoma (preferably colon carcinoma) and mammary carcinoma (preferably triple negative breast cancer).

In a preferred embodiment of the invention herein disclosed, the tumor diseases are prostate cancer. In a preferred embodiment of the invention herein disclosed, the prostate cancer is an adenocarcinoma. In a preferred embodiment of the invention herein disclosed, the tumor diseases are prostate cancer with mutated, absent or reduced expression of the AR. In this manner, the prostate cancer that may be treated according to the invention may be or have become resistant to anti-androgen targeted therapy, such as enzalutamide.

In a preferred embodiment of the invention herein disclosed, the exocrine pancreatic carcinoma is an adenocarcinoma. In a preferred embodiment the exocrine pancreatic cancer with absent or reduced expression of the AR.

In a preferred embodiment mammary carcinoma is triple negative breast cancer (TNBC). Optionally, the subject or patient being treated is a non-responder or relapse to conventional therapy.

In another object of the present invention said pharmaceutical composition comprises cortexolone 17 α-benzoate for use in the manufacture of a medicament for the treatment of precancerous lesions, dysplasias, metaplasias and tumor diseases, including malignant neoplasias and metastasis; according to another aspect, such a treatment may be curative, adjuvant, neoadjuvant or palliative.

In a further object, said pharmaceutical composition is for use as a Glucocorticoid Receptor (GR) modulator, preferably a glucocorticoid antagonist.

In another aspect, the invention relates to said pharmaceutical composition for use in the manufacture of a medicament for treating a disease or disorder mediated by glucocorticoid.

In a most preferred object, said pharmaceutical composition comprises cortexolone 17 α-benzoate.

According to another embodiment, said pharmaceutical composition may contain at least another active ingredient, preferably a chemotherapeutic active ingredient, optionally as a combination, for simultaneous, separate or sequential administration.

The pharmaceutical compositions of the invention can be in solid form, such as, by way of example, powders, freeze-dried powders, granules, pellets, tablets or capsules. If desired, certain sweetening, flavoring or coloring agents may also be added. The compounds of the invention can also be in microencapsulated form with one or more excipients. The solid dosage forms of tablets, capsules, pills, and granules can be prepared with coatings and shells such as enteric coatings and other coatings well known in the pharmaceutical formulating art. Appropriate excipients for solid pharmaceutical compositions can be selected, without any limitation, among the categories known to a person skilled in the art such as adsorbents, fillers, surfactants, compression aids, binders, lubricants, disintegrants, diluents, disgregants, flow promoting agents, freeze-drying agents, glidants, lyophilization aids, film-forming agents, dyes, antioxidants, and the like. By way of example, suitable excipients for solid pharmaceutical compositions can be selected, in a non-limiting way, from calcium phosphate, magnesium stearate, talc, sugars, lactose, dextrin, starch, gelatin, cellulose and derivatives thereof, polyvinylpyrrolidone, coating agents, dyes and wax. Any mixture of these excipients can be properly used according to the invention.

According to the invention, solid pharmaceutical compositions such as tables, granules, pellets, capsules and the like, can be formulated as immediate release forms or as delayed release forms or as controlled release forms or as extended release forms or as prolonged release forms, and are suitable for administration by the oral, or sublingual administration route or as an implant.

The controlled, extended and/or prolonged composition may be prepared according to any conventional method or system, for instance according to WO00/76478 herein incorporated by reference entirely.

The pharmaceutical compositions of the invention can also be in liquid form, for example, solutions, emulsions, suspensions or syrups.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art. Besides inert diluents, the oral compositions can also include adjuvants such as wetting agents, emulsifying and suspending agents, sweetening, flavoring, and perfuming agents.

Appropriate excipients for liquid pharmaceutical composition can be selected, without any limitation, among the categories well known to a person skilled in the art, such as solvents, co-solvents, oleaginous vehicles, buffering agents, surfactants, emulsifying agents, solubility enhancing agents, suspending agents, solubilizing agents, chelating agents, acidifying agents, alkalinizing agents, antioxidants, preservatives, osmotic agents, tonicity agents, viscosity controlling agents and the like. Bay way of example, suitable pharmaceutical excipients for liquid preparation can be selected from water for injections, organic solvents or co-solvents such as ethanol, glycols and glycerol and mixtures thereof, natural oils such as soybean oil, medium-chain triglycerides, polyoxyl 15-hydroxystearate, polysorbate 80, polyoxyl 35-castor oil, sodium chloride, sodium phosphate, potassium phosphate, and the like. According to the invention, said liquid pharmaceutical compositions can be sterile or non-sterile. In one embodiment, the liquid pharmaceutical compositions are terminally sterilized by means of a technique well known to a person skilled in the art, such as dry heat sterilization, moist heat sterilization, gamma radiation, e-beam sterilization and the like. In another embodiment, the liquid pharmaceutical compositions are sterilized by sterile filtration and aseptically filled in the final primary packaging containers. The liquid pharmaceutical compositions according to the invention herein disclosed can be used for injections, infusions or perfusions such as intravenous, intramuscular, intraperitoneal, subcutaneous or intratumoral administration.

Administration Methods

The compounds and pharmaceutical compositions described herein may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intra-articular, intrasynovial, intrasternal, intrathecal, intrahepatic, intralesional and intracranial injection or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Sterile injectable forms of the compounds and compositions described herein may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally-acceptable diluent or solvent.

The compounds for use in the methods of the invention can be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier.

The unit dosage form can be for a single daily dose or one of multiple daily doses (e.g., about 1 to 4 or more times per day). When multiple daily doses are used, the unit dosage form can be the same or different for each dose.

According to the invention, the compounds of formula (I) or the pharmaceutical compositions comprising the said compounds are preferably administered by intravenous injection, more preferably through an infusion bag or a syringe or a pump catheter, or by intramuscular injection, or by subcutaneous injection, or per os (by mouth) in forms of tablets or capsules.

According to an embodiment, said pharmaceutical composition is in liquid form and is suitable for injection, and comprise a cortexolone-derived compound of formula (I) in an amount ranging from 0.1% to 50.0% weight to volume (w/v), preferably from 0.25% to 25% w/v, more preferably from 0.5% to 10% w/v, much more preferably from 1% to 5% w/v.

According to another embodiment, said pharmaceutical composition is in solid form and comprises a cortexolone-derived compound of formula I in an amount ranging from 0.1% to 50% weight to weight (w/w), preferably from 0.5% to 40% w/w, more preferably from 1% to 30% w/w.

The amount of the at least one compound of formula (I) in said pharmaceutical composition is such that an effective dosage level can be obtained upon administration to a mammal suffering of precancerous lesions, dysplasias, metaplasias and tumor diseases, including malignant neoplasias and metastasis.

The compounds of formula (I) and the pharmaceutical composition comprising the same as antitumor active ingredients for use in the curative or adjuvant, or neoadjuvant or palliative treatment of precancerous lesions, dysplasias, metaplasias and tumor diseases, including malignant neoplasias and metastasis, are preferably administered to a mammal, said mammal being a human or an animal, preferably a human.

Combination Therapy

According to another embodiment, the compounds cortexolone 17α-benzoate (CB-03-06), cortexolone 17α-valerate (CB-03-05) and pharmaceutical composition comprising said compounds may contain at least another active ingredient, preferably a chemotherapeutic active ingredient, as a combination for simultaneous, separate or sequential administration.

In certain embodiments, the compounds of formula (I) and the pharmaceutical composition comprising at least one compound of formula (I) and at least one physiologically acceptable excipient according to the invention can be used in combination therapy with at least one other drug, especially a chemotherapeutic drug. In certain embodiments, the compounds of the invention can be administered concurrently with the administration of another drug, especially a chemotherapeutic drug. In certain embodiments, the compounds of the invention can be administered prior to or subsequent to administration of another drug, especially a chemotherapeutic drug. Said at least one other drug, especially a chemotherapeutic drug, can be effective for treating the same or different disease, disorder, or condition. Methods of the present invention include administration of one or more compounds of formula (I) or pharmaceutical compositions comprising at least a compound of formula (I) of the present invention and at least another drug, preferably a chemotherapeutic drug, provided that the combined administration does not inhibit the therapeutic efficacy of the one or more compounds of the present invention and/or does not produce non-acceptable adverse combination effects.

Cortexolone 17α-valerate (Herein also Referred to as "05" or as "CB-03-05")

As described above, another object of the present invention is cortexolone 17α-valerate (herein also referred to as "05" or as "CB-03-05"), represented by:

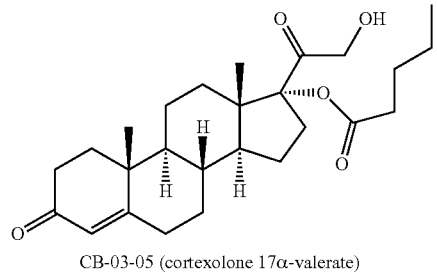

CB-03-05 (cortexolone 17α-valerate)

for use as a medicament.

Ideally, cortexolone 17α-valerate is for use in the treatment of precancerous lesions, dysplasias, metaplasias and tumor diseases, optionally including malignant neoplasias and metastasis. Preferably, cortexolone 17α-valerate is for use as an anti-tumor agent. Preferably, the tumor diseases are solid tumors, preferably epithelial tumors. The epithelial tumors may be selected from prostate carcinoma; mammary carcinoma; pancreatic carcinoma (preferably exocrine pancreatic cander); lung carcinoma; gastrointestinal tract carcinoma, such as colon carcinoma; kidney cancer; thyroid carcinoma; uterine carcinoma; and adrenal carcinoma.

According to one embodiment, the epithelial tumor is a prostate carcinoma. In another preferred embodiment of the invention, the tumor diseases are prostate cancer with mutated or truncated Androgen Receptors. In this manner, the prostate cancer that may be treated according to the invention may be or have become resistant to anti-androgen targeted therapy, such as enzalutamide.

According to another embodiment, the epithelial tumors are pancreatic carcinoma, preferably exocrine pancreatic carcinoma.

According to one embodiment, the epithelial tumors are mammary carcinoma, preferably triple negative breast cancer (TNBC). In one embodiment, the mammary carcinoma is triple negative breast cancer and the subject is a relapsed or a non-responder to conventional therapy.

According to another embodiment, the epithelial tumors are gastrointestinal tract carcinoma, such as colon carcinoma.

According to another embodiment, cortexolone 17α-valerate is for use as a Glucocorticoid Receptor (GR) modulator, preferably a glucocorticoid antagonist.

According to another aspect, there is provided a pharmaceutical composition comprising a compound of the following structural formula:

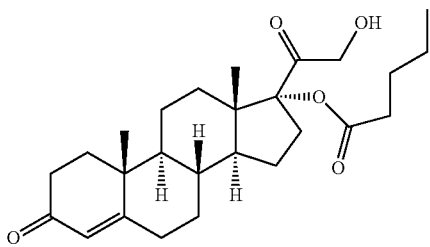

and at least one physiologically acceptable excipient for use as a medicament, preferably in the treatment of precancerous lesions, dysplasias, metaplasias and tumor diseases, optionally including malignant neoplasias and metastasis. Preferably said tumor diseases are solid tumors, preferably epithelial tumors, such as prostate carcinoma; mammary carcinoma; pancreatic carcinoma; lung carcinoma; gastrointestinal tract carcinoma, such as colon carcinoma; kidney cancer; thyroid carcinoma; uterine carcinoma; adrenal carcinoma.

According to another embodiment, said epithelial tumor is prostate carcinoma. In another preferred embodiment of the invention, the tumor diseases are prostate cancer with mutated or truncated Androgen Receptors. In this manner, the prostate cancer that may be treated according to the invention may be or have become resistant to anti-androgen targeted therapy, such as enzalutamide.

According to another embodiment, the epithelial tumors are pancreatic carcinoma, preferably exocrine pancreatic carcinoma.

According to another embodiment, the epithelial tumors are mammary carcinoma, preferably triple negative breast cancer (TNBC). In one embodiment, the mammary carcinoma is triple negative breast cancer and the subject is a relapsed or a non-responder to conventional therapy.

According to another embodiment, the epithelial tumors are gastrointestinal tract carcinoma, such as colon carcinoma.

The pharmaceutical composition may also comprise at least one other active ingredient, preferably a chemotherapeutic active ingredient, for simultaneous, separate or sequential administration.

According to another aspect, there is provided a pharmaceutical composition comprising a compound of the following structural formula:

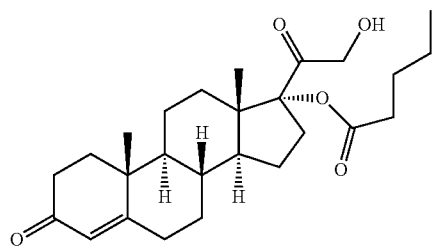

and at least one physiologically acceptable excipient for use as a Glucocorticoid Receptor (GR) modulator, preferably a glucocorticoid antagonist.

In another aspect, there is provided a method of treating precancerous lesions, dysplasias, metaplasias and tumor diseases in a subject in need thereof, comprising administrating a therapeutically effective amount of a compound of the following structural formula:

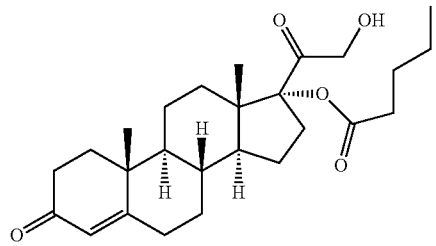

or a pharmaceutical composition comprising said compound to said subject.

According to one embodiment, the tumor diseases are malignant neoplasias or metastasis.

Preferably, the subject is a mammal. Ideally, the mammal is a human.

According to one embodiment, the tumor diseases are solid tumors. Optionally, the solid tumors are epithelial tumors. The epithelial tumors may be selected from prostate carcinoma, mammary carcinoma, uterine carcinoma, pancreatic carcinoma, lung carcinoma, gastro-intestinal tract carcinoma (preferably colon carcinoma), kidney cancer, thyroid carcinoma, uterine carcinoma and adrenal carcinoma and the like.

According to another embodiment, the epithelial tumors are prostate carcinoma, pancreatic carcinoma, exocrine pancreatic carcinoma, or mammary carcinoma. According to another embodiment, said epithelial tumor is prostate carcinoma. In another preferred embodiment of the invention, the tumor diseases are prostate cancer with mutated or truncated Androgen Receptors. In this manner, the prostate cancer that may be treated according to the invention may be or have become resistant to anti-androgen targeted therapy, such as enzalutamide.

According to another embodiment, the epithelial tumors are pancreatic carcinoma, preferably exocrine pancreatic carcinoma.

According to another embodiment, wherein the mammary carcinoma is triple negative breast cancer. In one embodiment, the mammary carcinoma is triple negative breast cancer and the subject is a relapsed or a non-responder to conventional therapy.

According to another embodiment, the epithelial tumors are gastrointestinal tract carcinoma, such as colon carcinoma.

According to another aspect of the invention, there is provided a method of treating a disease or disorder mediated by glucocorticoid, in a subject in need thereof, the method comprising administrating a therapeutically effective amount of cortexolone 17α-valerate or a pharmaceutical composition comprising cortexolone 17α-valerate.

EXAMPLES

Example 1: In-Vitro Antitumor Activity of Cortexolone 17α-benzoate (CB-03-06) on Prostate Cancer Cell Lines The experiment was performed to test and to define the antitumor activity in vitro of cortexolone 17α-benzoate on LNCaP (AR$^+$) and PC3 (AR$^-$), representative of Prostatic cancer cell lines with Androgen receptor positive or negative expression, respectively. The experimental method consisted of:

1. 3000 cancer cells were seeded in 96-well flat bottom plates in complete media containing 2% charcoal stripped bovine serum.
2. After 24 hrs, 10 nM DHT (dihydrotestosterone) with or without anti-androgen compounds, or DMSO vehicle (negative control) was added to the cultures.
3. After 3 days, viable cell numbers were quantitated using an ATP-dependent proliferation assay.

The aim of the test was to determine the concentration at which each compound kills 50% of the cancer cells ($IC_{50}$) in view of a potential application of the compound in in vivo animal test.

Data from Experiment 1 was fitted through sigmoidal dose response curves and analyzed using Prizm statistical analysis software. Data from Experiment 2 were s analyzed using nonlinear regression least squares curve fit in Prizm statistical analysis software. The $IC_{50}$ value found for each line is reported in the following table, compared to well known comparators currently used in the treatment of prostatic cancer: the most potent anti-androgenic steroid, Cyproterone Acetate (CPA), and Enzalutamide, an oral androgen-receptor inhibitor able to prolong survival in men with metastatic castration-resistant prostate cancer. The results from 2 sets of experiments follow.

Experiment 1

The results were fitted through sigmoidal dose response curves in Prizm statistical analysis software.

| Tumour Cell lines | CB-03-06 [Cortexolone 17α-benzoate] | Cyproterone Acetate | Enzalutamide |
|---|---|---|---|
| LNCaP | 12 | 29 | 40 |
| PC 3 | 29 | 98 | 208 |

Experiment 2

The results below include additional experiments to those in Experiment 1. The results were analyzed using nonlinear regression least squares curve fit in Prizm statistical analysis software.

| Tumor Cell lines | $IC_{50}$ (microM) CB-03-06 [Cortexolone 17α-benzoate] | $IC_{50}$ (microM) Cyproterone Acetate $IC_{50}$ | $IC_{50}$ (microM) Enzalutamide |
|---|---|---|---|
| LNCaP | 12 | 22 | 38 |
| PC3 | 28 | 90 | 180 |

$IC_{50}$ values show that the antitumor activity of Cortexolone 17α-benzoate, even though with a weak correlation trend, could be considered not strictly dependent on the Androgen Receptor expression, differently from the comparators.

Example 2: In-Vitro Antitumor Activity of Cortexolone 17α-valerate-21-propionate (CB-03-10) on Prostate Cancer Cell Lines The experiment was performed to test and to define antitumor activity in vitro of cortexolone 17α-valerate-21-propionate on LNCaP (AR$^+$) and PC3 (AR$^-$), representative of Prostatic cancer cell lines with Androgen receptor positive or negative expression, respectively. The experimental method consisted of:

1. 3000 cancer cells were seeded in 96-well flat bottom plates in complete media containing 2% charcoal stripped bovine serum.
2. After 24 hours, 10 nM DHT (dihydrotestosterone) with or without anti-androgen compounds, or DMSO vehicle (negative control) was added to the cultures.
3. After 3 days, viable cell numbers were quantitated using an ATP-dependent proliferation assay.

The aim of the test was to determine the concentration at which each compound kills 50% of the cancer cells ($IC_{50}$) in view of a potential application of the compound in in vivo animal test.

Data from Experiment 1 was fitted through sigmoidal dose response curves and analyzed using Prizm statistical analysis software. Data from Experiment 2 were analyzed using nonlinear regression least squares curve fit in Prizm statistical analysis software. The $IC_{50}$ value found for each line is reported in the following table, compared to well known comparators currently used in the treatment of prostatic cancer: the most potent anti-androgenic steroid, Cyproterone Acetate (CPA), and Enzalutamide, an oral androgen-receptor antagonist able to prolong survival in men with metastatic castration-resistant prostate cancer. The results from 2 sets of experiments follow.

Experiment 1

The results were fitted through sigmoidal dose response curves in Prizm statistical analysis software.

| Tumour Cell lines | CB-03-10 [Cortexolone 17α-valerate-21-propionate] | Cyproterone Acetate | Enzalutamide |
|---|---|---|---|
| LNCaP | 13 | 29 | 40 |
| PC 3 | 55 | 98 | 208 |

Experiment 2

The results below include additional experiments to those in Experiment 1. The results were analyzed using nonlinear regression least squares curve fit in Prizm statistical analysis software.

| Tumor Cell lines | IC$_{50}$ (microM) CB-03-10 [Cortexolone 17α-valerate-21-propionate] | IC$_{50}$ (microM) Cyproterone Acetate IC$_{50}$ | IC$_{50}$ (microM) Enzalutamide |
|---|---|---|---|
| LNCaP | 10 | 22 | 38 |
| PC 3 | 50 | 90 | 180 |

IC$_{50}$ values show that the antitumor activity of Cortexolone 17α-valerate-21-propionate (CB-03-10) could correlate with the Androgen Receptor expression in the cell lines.

Example 3: In-Vitro Antitumor Activity of Cortexolone 17α-Benzoate (CB-03-06) on Pancreatic Cancer Cell Lines The experiment was performed to test and to define the antitumor activity in vitro of cortexolone 17α-benzoate on two pancreatic tumor cell lines, Panc1 (AR$^+$) and MiaPaca2 (AR low), representative of Pancreatic cancer cells.

The lines were also classified as positive (AR$^-$) or low (AR$^{+/-}$)/negative (AR$^-$) for the presence and expression of the Androgen Receptor.

The experimental method consisted of:
1. 3000 cancer cells were seeded in 96-well flat bottom plates in complete media containing 2% charcoal stripped bovine serum
2. After 24 hrs, 10 nM DHT (dihydrotestosterone) with or without anti-androgen compounds, or DMSO vehicle (negative control) was added to the cultures.
3. After 3 days, viable cell numbers were quantitated using an ATP-dependent proliferation assay.

The aim of the test was to determine the concentration at which each compound kills 50% of the cancer cells (IC$_{50}$) in view of a potential application of the compound in in vivo animal test.

Data from Experiment 1 were fitted through sigmoidal dose response curves and analyzed using Prizm statistical analysis software. Data from Experiment 2 were analyzed using nonlinear regression least squares curve fit in Prizm statistical analysis software. The IC$_{50}$ value found for each line is reported in the following table, compared to well known comparators currently used in the treatment of prostatic cancer: the most potent anti-androgenic steroid, Cyproterone Acetate (CPA), and Enzalutamide, an oral androgen-receptor antagonist able to prolong survival in men with metastatic castration-resistant prostate cancer. The results from 2 sets of experiments follow.

Experiment 1

The results were fitted through sigmoidal dose response curves in Prizm statistical analysis software.

| Tumour Cell lines | CB-03-06 [Cortexolone 17α-benzoate] | Cyproterone Acetate | Enzalutamide |
|---|---|---|---|
| Panc1 | 30 | 54 | 156 |
| MiaPaca2 | 23 | 46 | 77 |

Experiment 2

The results below include additional experiments to those in Experiment 1. The results were analyzed using nonlinear regression least squares curve fit in Prizm statistical analysis software.

| Tumor Cell lines | IC$_{50}$ (microM) CB-03-06 [Cortexolone 17α-benzoate] | IC$_{50}$ (microM) Cyproterone Acetate IC$_{50}$ | IC$_{50}$ (microM) Enzalutamide |
|---|---|---|---|
| Panc1 | 28 | 46 | 111 |
| MiaPaca2 | 20 | 39 | 65 |

IC$_{50}$ values show that the antitumor activity of Cortexolone 17α-benzoate (CB-03-06) is at least twice higher than the activity of the comparators (CPA and Enzalutamide), and that no correlation exists with the Androgen Receptor expression in the cell lines. Since MiaPaca2 are characterized by a low/null AR expression, the anti-cancer activity of the compound is not directly correlated to the Androgen Receptor expression in the cancer cell lines.

Example 4: In Vitro Antitumor Activity of Cortexolone 17α-valerate-21-propionate (CB-03-10) on Pancreatic Cancer Cell Lines The experiment was performed to test and to define the antitumor activity in vitro of cortexolone 17α-valerate-21-propionate on cell lines representatives of pancreatic tumors, namely Panc1 (AR$^+$) and MiaPaca2 (R low), representative of Pancreatic cancer cells.

The lines were also classified as positive (AR$^+$) or low (AR$^{+/-}$)/negative (AR$^-$) for the presence and expression of the Androgen Receptor.

The experimental method consisted of:
1. 3000 cancer cells were seeded in 96-well flat bottom plates in complete media containing 2% charcoal stripped bovine serum
2. After 24 hrs, 10 nM DHT (dihydrotestosterone) with or without anti-androgen compounds, or DMSO vehicle (negative control) was added to the cultures.
3. After 3 days, viable cell numbers were quantitated using an ATP-dependent proliferation assay.

The aim of the test was to determine the concentration at which each compound kills 50% of the cancer cells (IC$_{50}$) in view of a potential application of the compound in in vivo animal test.

Data from Experiment 1 was fitted through sigmoidal dose response curves and analyzed using Prizm statistical analysis software. Data from Experiment 2 were analyzed using nonlinear regression least squares curve fit in Prizm statistical analysis software.

The IC$_{50}$ value found for each line is reported in the following table, compared to well known comparators: the most potent anti-androgenic steroid, Cyproterone Acetate (CPA), and Enzalutamide, an oral androgen-receptor antagonist able to prolong survival in men with cancer. The results from 2 sets of experiments follow.

Experiment 1

The results were fitted through sigmoidal dose response curves in Prizm statistical analysis software.

| Tumour Cell lines | CB-03-10 [Cortexolone 17α-valerate-21-propionate] | Cyproterone Acetate | Enzalutamide |
|---|---|---|---|
| Panc1 | 66 | 54 | 156 |
| MiaPaca2 | 43 | 46 | 77 |

Experiment 2

The results below include additional experiments to those in Experiment 1. The results were analyzed using nonlinear regression least squares curve fit in Prizm statistical analysis software.

| Tumor Cell lines | $IC_{50}$ (microM) CB-03-10 [Cortexolone 17α-valerate-21-propionate] | $IC_{50}$ (microM) Cyproterone Acetate $IC_{50}$ | $IC_{50}$ (microM) Enzalutamide |
|---|---|---|---|
| Panc1 | 60 | 46 | 111 |
| MiaPaca2 | 37 | 39 | 65 |

$IC_{50}$ values show that the antitumor activity of Cortexolone 17α-valerate-21-propionate is not correlated with the Androgen Receptor expression on the cell lines.

Example 5: In-Vivo Human Pancreatic Tumor Xenograft in Mice

The activity of cortexolone 17α-benzoate (CB-03-06) on pancreatic xenograft tumor growth in nude mice has been evaluated in comparison with the most potent anti-androgenic steroid Cyproterone Acetate (CPA).

Cortexolone 17α-benzoate and Cyproterone Acetate were separately diluted in DMSO/2-hydroxypropyl β-cyclodextrin (vehicle).

The test was carried out comparing the anti-tumor activity of cortexolone 17α-benzoate at two different dosages (8.0 mg/kg, corresponding approximately at 230 µM, and 40 mg/kg, corresponding approximately at 1150 µM), versus the vehicle (i.e. 0.4% (v/v) tween 80 and 0.5% (w/v) carboxymethylcellulose in normal saline) and versus the comparator Cyproterone Acetate at two different dosages (7.4 mg/kg and 37 mg/kg).

$1\times10^6$ MiaPaca-2 cells suspended in matrigel were subcutaneously injected into 6 week old athymic nude mice.

The treatment with the tested compounds, with the vehicle and with the comparative compound, was initiated after the tumor volume has reached 50 $mm^3$ after transplantation. All compounds were injected 100 µL/mouse of low dose solution (approximately 230 µM) or 100 µL/mouse of high dose solution (approximately 1150 µM) of cortexolone 17α-benzoate, vehicle and Cyproterone Acetate, respectively. Compounds and controls were administered subcutaneously daily for 28 days.

Tumors were measured every 4 days with a digital caliper.

The results are plotted in FIG. 1 as average change in tumor volume relative to the start of treatment. Tumor volume was calculated according to the formula $0.5236(r_1)^2(r_2)$ where $r_1<r_2$.

Error bars are the SEM for 7 to 10 mice per treatment group. P values were calculated according to the Student's t test.

The high does of Cortexolone 17α-benzoate maintained the pancreatic tumor size to less than 5-fold the size of the tumor when treatment was initiated. In contrast, the average tumor in the vehicle and in the Cyproterone Acetate treatment groups increased in size to 12-fold. From these data the anti-tumoral activity of the compound of the present invention, cortexolone 17α-benzoate, is evident.

Example 6: In-Vivo Human Pancreatic Tumor Xenograft in Mice

The activity of cortexolone 17α-valerate-21-propionate (CB-03-10) on xenograft model of pancreatic tumor in nude mice has been evaluated in comparison with the anti-androgenic steroid Cyproterone Acetate (CPA).

Cortexolone 17α-valerate-21-propionate and Cyproterone Acetate were separately diluted in DMSO/2-hydroxypropyl β-cyclodextrin (vehicle).

The test was carried out comparing the anti-tumor activity of cortexolone 17α-valerate-21-propionate at two different dosages (approximately 8.6 mg/kg and 43 mg/kg) versus the vehicle (i.e. 0.4% (v/v) tween 80 and 0.5% (w/v) carboxymethylcellulose in normal saline) and versus the comparator Cyproterone Acetate at two different dosages (7.4 mg/kg and 37 mg/kg).

$1\times10^6$ MiaPaca-2 cells suspended in matrigel were subcutaneously injected into 6 week old athymic nude mice.

The treatment with the tested compound, with the vehicle and with the comparative compound was initiated after the tumor has reached a volume of 50 $mm^3$ after implantation, injecting subcutaneously 100 µL/mouse of low dose solution (approximately 230 µM) or 100 µL/mouse of high dose solution (approximately 1150 µM) of cortexolone 17α-valerate-21-propionate, vehicle and Cyproterone Acetate, respectively. Compounds and controls were administered subcutaneously daily for 28 days. Tumors were measured every 4 days with a digital caliper.

Figure 2:
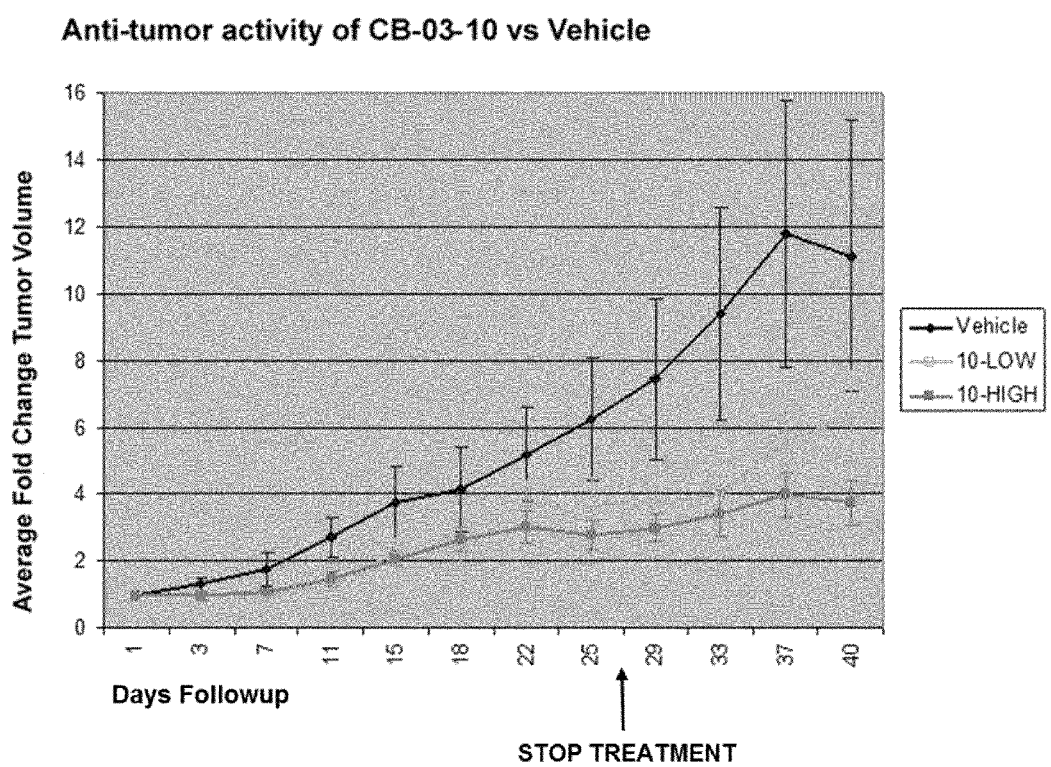
FIG. 2: Average change in pancreatic tumor volume, measured relatively to the start of treatment, in the xenograft animal model of nude mice (MiaPaca pancreatic cell line) with cortexolone 17α-valerate-21-propionate (in the figure referred to as "10" and as "CB-03-10") at low dose (230 μM) and at high dose (1150 μM). Reference to "Vehicle" is a control treated group with 0.4% (v/v) tween 80 and 0.5% (w/v) carboxymethylcellulose in normal saline. Mice were treated with the compound and vehicle SC daily for 28 consecutive days. The stop treatment arrow refers to the day when the treatment was ended.

The results are plotted in FIG. 2 as average change in tumor volume relative to the start of treatment. Tumor volume was calculated according to the formula $0.5236(r_1)^2(r_2)$ where $r_1<r_2$.

Error bars are the SEM for 7 to 10 mice per treatment group. P values were calculated according to the Student's t test.

Cortexolone 17α-valerate-21-propionate maintained the pancreatic tumor size increased to less than 5-fold the initial tumor size for the time of treatment. Moreover, when the treatment has been stopped, the tumor size tended to increase again, but with a lower rate and extent. In contrast, the average tumor in the vehicle and in the Cyproterone Acetate treatment groups increased in size to 12-fold and more, bringing to the need of suppressing some of the animal of these groups for human reasons. From these data the antitumor activity of the compound of the present invention, cortexolone 17α-valerate-21-propionate, is evident.

Figure 3:
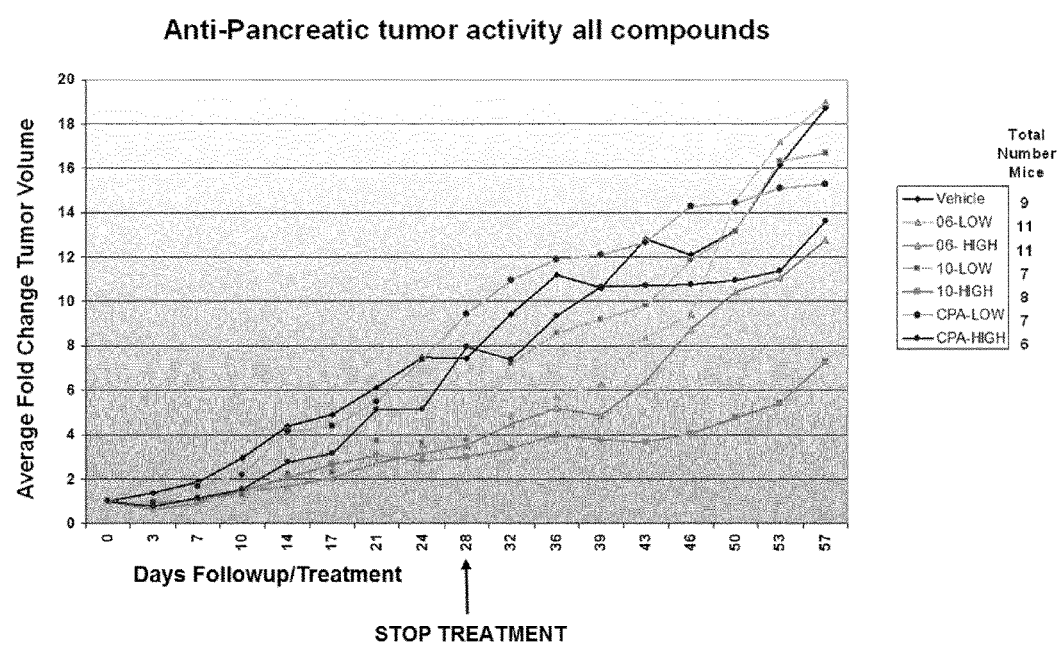
FIG. 3: average change in pancreatic tumor volume relative to the start of treatment in the animal model of nude mice (MiaPaca pancreatic cell line) treated with Cyproterone Acetate (in the figure referred to as CPA), cortexolone 17α-valerate-21-propionate (in the figure referred to as "10") and cortexolone 17α-benzoate (in the figure referred to as "06") (each compound at low dose and at high dose) and with vehicle (i.e. 0.4% (v/v) tween 80 and 0.5% (w/v) carboxymethylcellulose in normal saline) treated control group. All mice were treated with the compound and vehicle SC daily for 28 consecutive days (days treatment). The stop treatment arrow refers to the day when the treatment was ended.
Figure 4:
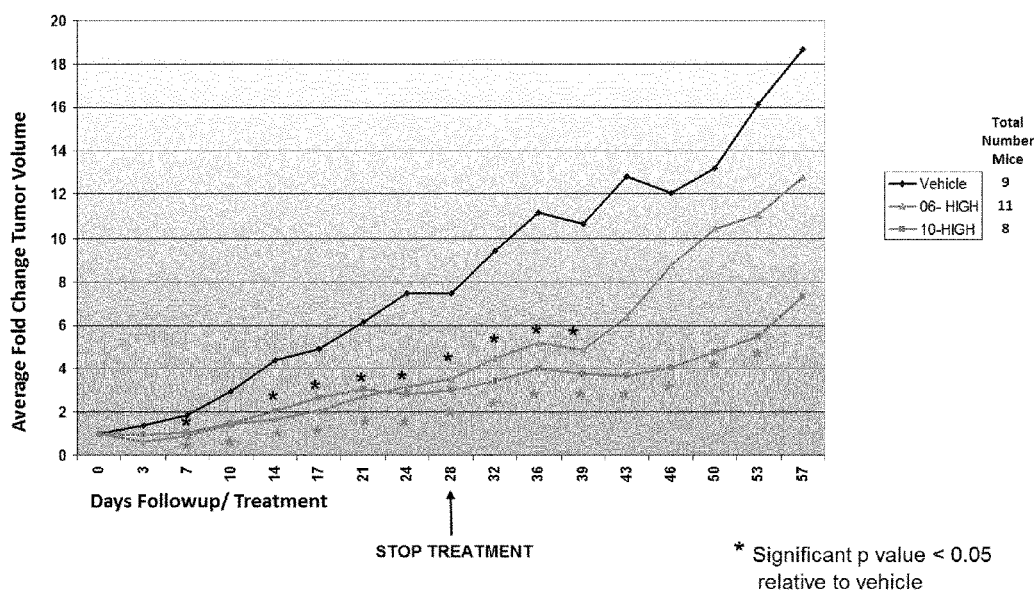
FIG. 4: Graph showing the P values Vs vehicle (i.e. 0.4% (v/v) tween 80 and 0.5% (w/v) carboxymethylcellulose in normal saline) treated control group of the best doses from FIG. 3. All mice were treated with the compound and vehicle SC daily for 28 consecutive days. The stop treatment arrow refers to the day when the treatment was ended (days treatment). The stop treatment arrow refers to the day when the treatment was ended.

From the data of Examples 5 and 6, the evident in vivo antitumor activity of cortexolone 17α-benzoate and cortexolone 17α-valerate-21-propionate against the pancreatic tumor was confirmed, and both the compounds resulted to have an antitumor activity higher than Cyproterone Acetate in the same animal model (see FIGS. 3 and 4).

Example 7: In-Vitro Therapeutic Index on Pancreatic Cancer Cells Lines

In order to evaluate the safety of the compounds to be tested in the cell lines viability experiments, all the factor impacting on the cell survival and viability should be taken into account. In this sense, the evaluation of intrinsic toxicity of compound and comparators is really important. The ratio from $IC_{50}$ of the compounds on peripheral blood mononuclear cells (PBMC) and the $IC_{50}$ on cancer cell lines constitute the Therapeutic Index and show what is the safer compound to be tested.

The $IC_{50}$ in PBMCs were tested in 2 different activation status:
   stimulated—actively dividing cells
   resting—quiescent, non-dividing cells Results are reported in the below tables, relevant to, respectively, stimulated PBMC and resting PBMC:

$IC_{50}$ (microM) on Stimulated PBMC

Experiment 1

| Cell lines | CB-03-06 [Cortexolone 17α-benzoate] | CB-03-10 [Cortexolone 17α-valerate, 21-propionate] | Cyproterone Acetate | Enzalutamide |
|---|---|---|---|---|
| Panc1 | 23 | 68 | 52 | 159 |
| MiaPaca2 | 17 | 34 | 39 | 79 |
| PBMC | 113 | 106 | 63 | 52 |

Experiment 2

| Cell lines | CB-03-06 [Cortexolone 17α-benzoate] $IC_{50}$ (microM) | CB-03-10 [Cortexolone 17α-valerate, 21-propionate] $IC_{50}$ (microM) | Cyproterone Acetate $IC_{50}$ (microM) | Enzalutamide $IC_{50}$ (microM) |
|---|---|---|---|---|
| Panc1 | 28 | 60 | 46 | 110 |
| MiaPaca2 | 20 | 37 | 39 | 65 |
| PBMC | 97 | 94 | 62 | 90 |

In parallel the same experiments have been repeated on resting PBMC, obtaining the results here below.

$IC_{50}$ (microM) on Resting PBMC

Experiment 1

| Cell lines | CB-03-06 [Cortexolone 17α-benzoate] | CB-03-10 [Cortexolone 17α-valerate, 21-propionate] | Cyproterone Acetate |
|---|---|---|---|
| Panc1 | 23 | 68 | 52 |
| MiaPaca2 | 17 | 34 | 39 |
| PBMC | 100 | 114 | 18 |

Experiment 2

| Cell lines | CB-03-06 [Cortexolone 17α-benzoate] $IC_{50}$ (microM) | CB-03-10 [Cortexolone 17α-valerate, 21-propionate] $IC_{50}$ (microM) | Cyproterone Acetate $IC_{50}$ (microM) |
|---|---|---|---|
| Panc1 | 28 | 60 | 46 |
| MiaPaca2 | 20 | 37 | 39 |
| PBMC | 85 | 120 | 84 |

The resulting Therapeutic Index (TI) calculated on Stimulated PBMC are reported in the table below:

TI on Stimulated PBMC

Experiment 1

| Cell lines | CB-03-06 [Cortexolone 17α-benzoate] | CB-03-10 [Cortexolone 17α-valerate, 21-propionate] | Cyproterone Acetate | Enzalutamide |
|---|---|---|---|---|
| Panc1 | 5 | 2 | 1 | 0 |
| MiaPaca2 | 7 | 3 | 2 | 1 |

Experiment 2

| Cell lines | CB-03-06 TI [Cortexolone 17α-benzoate] | CB-03-10 TI [Cortexolone 17α-valerate, 21-propionate] | Cyproterone Acetate TI | Enzalutamide TI |
|---|---|---|---|---|
| Panc1 | 3 | 2 | 1 | 1 |
| MiaPaca2 | 5 | 3 | 2 | 1 |

The resulting Therapeutic Index calculated on resting PBMC is reported in the table below:

TI on Resting PBMC

Experiment 1

| Cell lines | CB-03-06 [Cortexolone 17α-benzoate] | CB-03-10 [Cortexolone 17α-valerate, 21-propionate] | Cyproterone Acetate |
|---|---|---|---|
| Panc1 | 4 | 2 | 0 |
| MiaPaca2 | 6 | 3 | 0 |

Experiment 2

| Cell lines | CB-03-06 TI [Cortexolone 17α-benzoate] | CB-03-10 TI [Cortexolone 17α-valerate, 21-propionate] | Cyproterone Acetate TI |
|---|---|---|---|
| Panc1 | 3 | 2 | 4 |
| MiaPaca2 | 4 | 3 | 1 |

In the tables, the 0 value indicates higher toxicity in PBMC than in the cancer cell lines Example 8: In-Vitro Antitumor Activity of Cortexolone 17α-benzoate and Cortexolone 17α-valerate, 21-propionate (CB-03-10) on Epithelial Intestinal Cancer Cell Lines The experiment was performed to test and define anticancer activity in vitro of Cortexolone 17α-benzoate and cortexolone 17α-valerate, 21-propionate on cell lines representatives of epithelial intestinal tumours, namely HT29. The experiment method consisted in:

1. Monolayer HT-29 cells were plated in: 96-wells plates at the density of 2×104 cells/mL. The cells plated were kept at 37° C. in 5% $CO_2$ and left to attach for 24 h.
2. Thereafter the cells were incubated for 72 h with the test compounds at the concentrations each of 0.16, 0.8, 4, 20, 100 and 500 mM.
3. After 72 h of treatment, the MTT colorimetric assay was performed.

The aim of the test was to determine the concentration at which each compound kills 50% of the cancer cells ($IC_{50}$) in view of a potential application of the compound in in vivo animal test.

Data were fitted through sigmoidal dose response curves and analyzed using Prizm statistical analysis software.

The $IC_{50}$ value found for each line is reported in the following table.

Inhibition (%) at Different Micromolar Concentration for the Two Products on HT29

| Micromolar concentrations | CB-03-10 [Cortexolone 17α-valerate, 21-propionate] | CB-03-06 [Cortexolone17α-benzoate] |
|---|---|---|
| 0.8 | 0.44% | −1.55% |
| 4 | 14.23% | 20.40% |
| 20 | 25.49% | 53.60% |
| 100 | 89.77% | 92.24% |
| 500 | 92.10% | 92.31% |

The $IC_{50}$ values calculated for the two product (reported here below) show that both compounds have an evident anticancer activity on the HT29.

$IC_{50}$ Calculated (Micromolar Concentration)

| | |
|---|---|
| CB-03-06 | 15.97 |
| CB-03-10 | 34.16 |

Example 9: In-Vitro Therapeutic Index on Epithelial Intestinal Cancer Cells Lines In order to evaluate the safety of the compounds to be tested in the cell lines viability experiments, all the factor impacting on the cell survival and viability should be taken into account. In this sense, the evaluation of intrinsic toxicity of compound and comparators is really important. The ratio between $IC_{50}$ of the compounds on PBMC and the $IC_{50}$ on cancer cell lines constitute the Therapeutic Index, a parameter important to define the product efficacy in safe conditions.

The $IC_{50}$ in PBMCs were tested in 2 different activation status:

Stimulated—actively dividing cells

Resting—quiescent, non-dividing cells.

The resulting Therapeutic Index (TI) calculated on Stimulated and Resting PBMC are reported in the hereunder table:

Experiment 1

| Product | CB-03-06 [Cortexolone 17α-benzoate] | CB-03-10 [Cortexolone 17α-valerate, 21-propionate |
|---|---|---|
| Stimulated | 7 | 3 |
| Resting | 6 | 3 |

Experiment 2

| Product | CB-03-06 (TI)[Cortexolone 17α-benzoate] | CB-03-10 (TI)[Cortexolone 17α-valerate, 21-propionate |
|---|---|---|
| Stimulated | 6 | 3 |
| Resting | 5 | 4 |

From these data the anti-tumoral activity and safety of the compound of the present invention, cortexolone 17α-valerate, 21-propionate, was confirmed versus the epithelial intestinal cancer cells.

Example 10—Synthesis of Cortexolone 17α-benzoate

Cortexolone 17α-benzoate was prepared according to a synthesis scheme including the following steps:

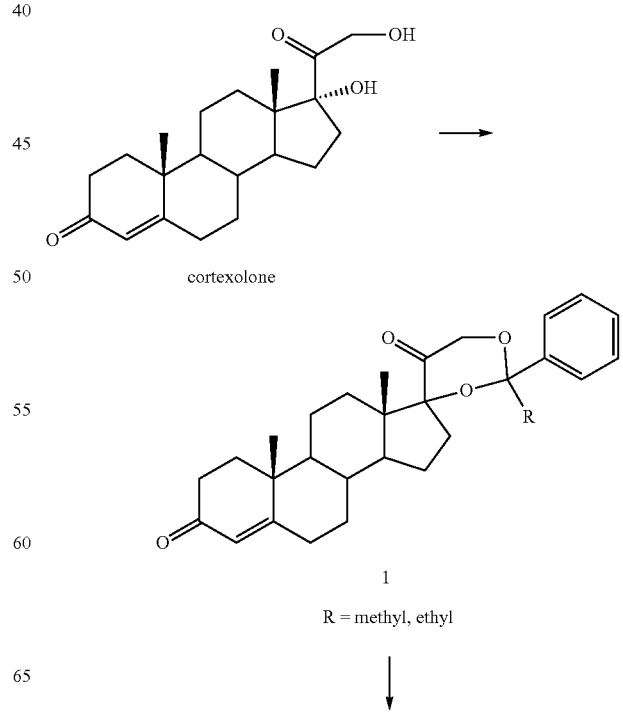

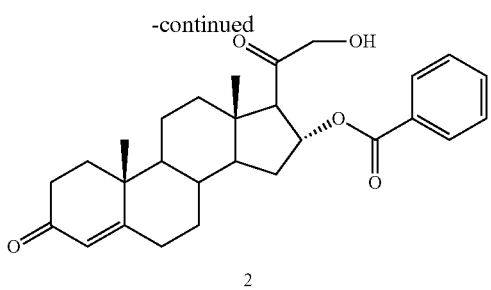

In Step 1 Cortexolone was dissolved in a suitable solvent (e.g. ethyl acetate). Pyridinium tosilate or p-toluene sulfonic acid was added in catalytic amount (1-10% mol) followed by tri-alkyl orthobenzoate (R=methyl or R=ethyl). The reaction mixture was heated up to 80° C. for 3 to 6 hours.

After removal of the solvent and crystallization in alcoholic solvent, cortexolone orthobenzoate 1 was obtained as a solid.

In Step 2, cortexolone orthobenzoate 1 (R=methyl or R=ethyl) was dissolved in an alcoholic solvent (e.g. methanol) and treated with 0.1N acetic buffer at reflux. After removal of the solvent, the residue was purified by treatment with demi water and cortexolone-17-α-benzoate was recovered as a solid.

Example 11: Synthesis of Cortexolone 17α-valerate-21-propionate

Cortexolone 17α-valerate-21-propionate was prepared according to the following synthetic scheme:

In Step 2, cortexolone orthovalerate 1 (R=methyl or R=ethyl) was dissolved in an alcoholic solvent (e.g. methanol) and treated with 0.1N acetic buffer (pH 3 to 3.9) at reflux. After the removal of the solvent followed by treatment with purified water, cortexolone-17α-valerate 2 was recovered as a solid.

In Step 3, cortexolone-17α-valerate 2 was dissolved in pyridine and added with 1 equivalent of propionyl chloride. When the conversion was complete, the mixture was diluted with water, and the product 3 was recovered as a solid and purified by crystallization with alcohols.

Example 12: Analysis of In Vitro Anti-Cancer Activity of Cortexolone Derived Compounds, in Particular CB-03-06

The capability of a series of cortexolone-derived compounds, an in particular CB-03-06, to inhibit the growth of cancer cell lines established in vitro was tested.

Figure 5:
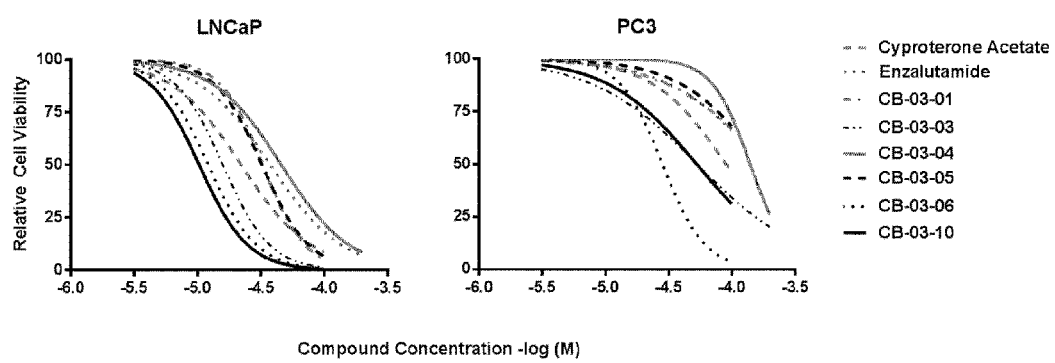
FIG. 5; Dose Titration of cytotoxicity of cortexolone-derived compounds in human prostate (a) and pancreatic (b) cancer cell lines.
Figure 5:
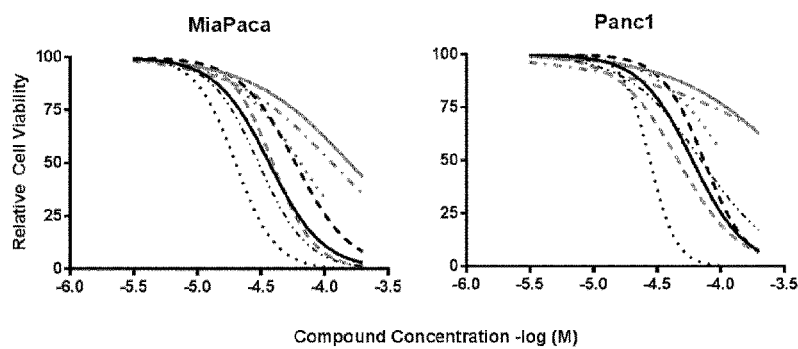

Cancer cell lines were seeded at 3000 cells in 96-well flat bottom plates in complete media containing 2% charcoal stripped bovine serum. After 24 hours the test compounds or DMSO/vehicle (0.1% final concentration as negative control) were added. Cyproterone acetate (CPA) and Enzalutamide, two potent recognized anti-androgens were used as positive control for cell cytotoxicity. After 3 days, viable cell numbers were quantitated using an ATP-dependent cell viability assay (Promega Cell Titer Glo). FIG. 5 shows a dose titration of the cytotoxicity activity of cortexolone derived compounds on human prostate and pancreatic cell lines. The determination of the concentration at which each compound kills 50% of the cancer cells ($IC_{50}$) was per-

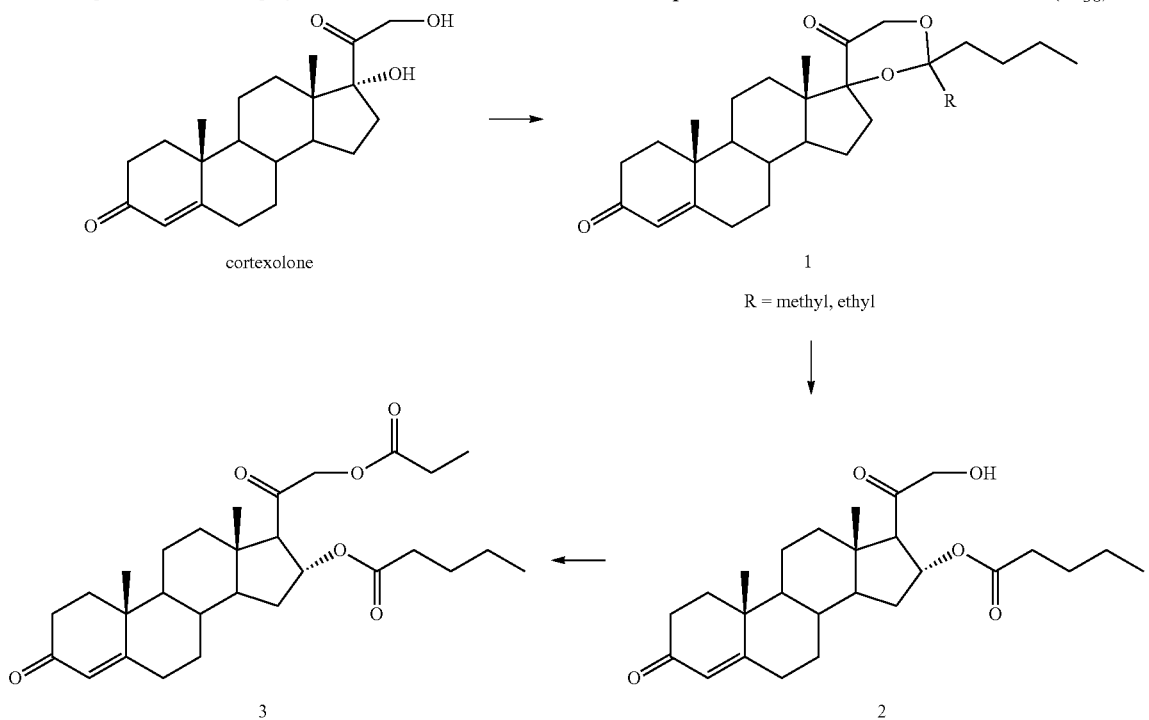

R = methyl, ethyl

Step 1: Cortexolone was dissolved in a suitable solvent (e.g. ethyl acetate). Pyridinium tosilate or p-toluene sulfonic acid was added in catalytic amount (1-10% mol) followed by tri-alkyl orthovalerate (R=methyl or R=ethyl). The reaction mixture was heated up to 80° C. for 3-5 hours and, after removal of the solvent and crystallization in alcoholic solvent, cortexolone orthovalerate 1 was obtained.

formed to express the capability of CB-03-06 and other compounds to inhibit cancer cell growth. Each compound was titrated from 3 uM to 200 uM. After 3 days, viable cell numbers were quantitated using an ATP-dependent proliferation assay. Data shown in Table I were fitted through sigmoidal dose response curves and analyzed using Prizm statistical.

TABLE I

IC$_{50}$ of Cortexolone-derived Compounds tested in vitro in Prostate & Pancreatic Cancer Cell Lines

| Tissue Type | Cell Line Name | CB-03-01 C17 prop | CB-03-03 C17,21 but | CB-03-04 9dehy 17 but | CB-03-05 C17 val | CB-03-06 C17 ben | CB-03-10 C17,21 val | Enza lutamide | CPA |
|---|---|---|---|---|---|---|---|---|---|
| Prostate Cancer | LNCaP | 33 | 16 | 46 | 32 | 12 | 10 | 38 | 22 |
|  | PC3 | 190 | 53 | 140 | 170 | 28 | 53 | 180 | 90 |
| Pancreatic Cancer | Panc1 | 490 | 70 | 340 | 74 | 28 | 60 | 110 | 46 |
|  | MiaPaca2 | 110 | 30 | 160 | 59 | 20 | 37 | 65 | 39 |

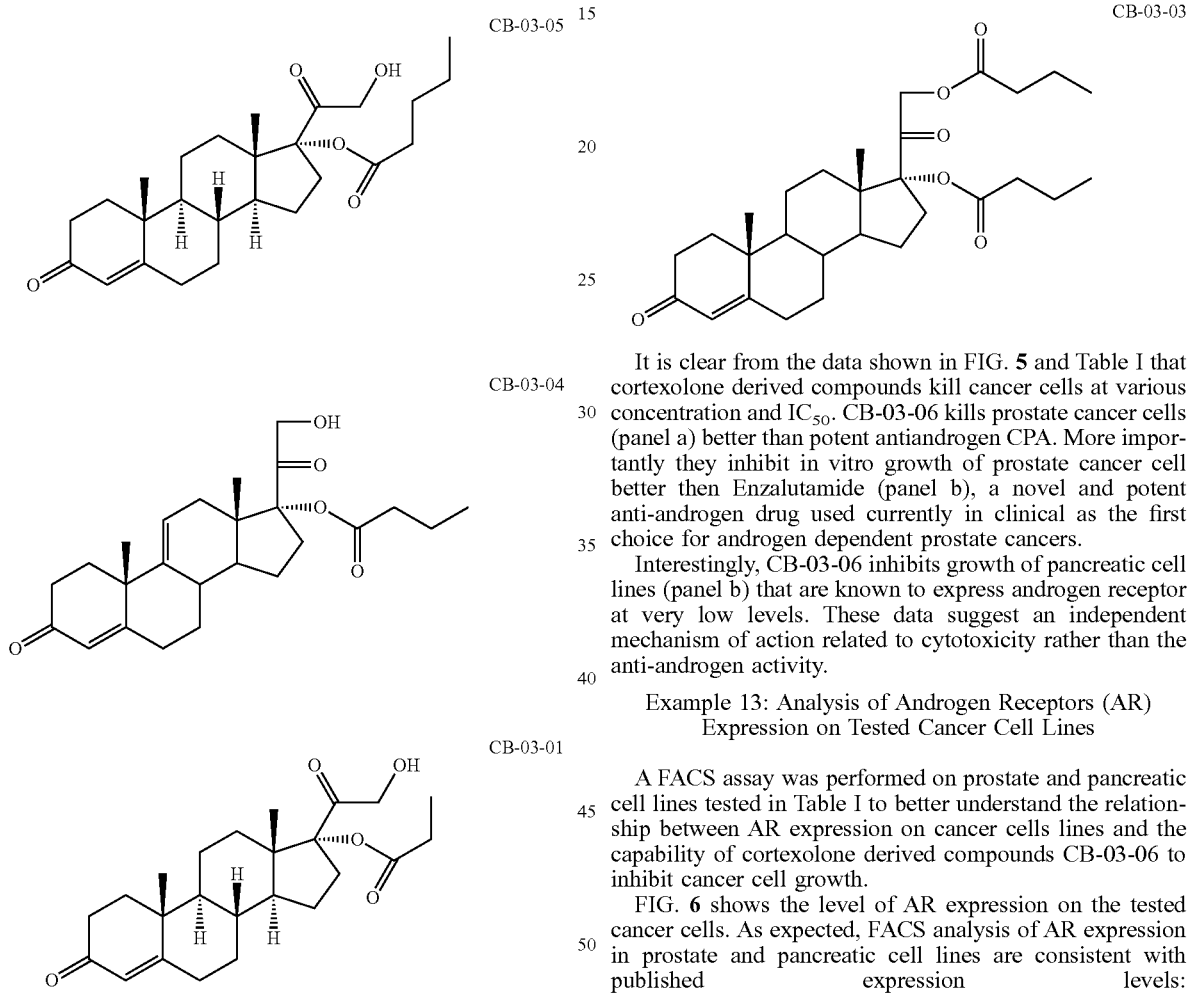

It is clear from the data shown in FIG. 5 and Table I that cortexolone derived compounds kill cancer cells at various concentration and IC$_{50}$. CB-03-06 kills prostate cancer cells (panel a) better than potent antiandrogen CPA. More importantly they inhibit in vitro growth of prostate cancer cell better then Enzalutamide (panel b), a novel and potent anti-androgen drug used currently in clinical as the first choice for androgen dependent prostate cancers.

Interestingly, CB-03-06 inhibits growth of pancreatic cell lines (panel b) that are known to express androgen receptor at very low levels. These data suggest an independent mechanism of action related to cytotoxicity rather than the anti-androgen activity.

Example 13: Analysis of Androgen Receptors (AR) Expression on Tested Cancer Cell Lines A FACS assay was performed on prostate and pancreatic cell lines tested in Table I to better understand the relationship between AR expression on cancer cells lines and the capability of cortexolone derived compounds CB-03-06 to inhibit cancer cell growth.

Figure 6:
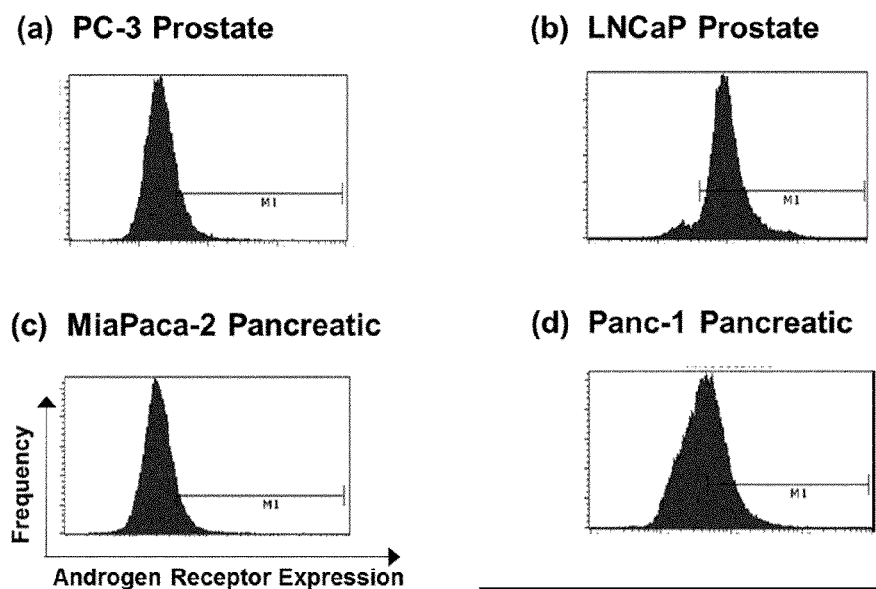
FIG. 6: AR Expression levels on cancer cell lines.

FIG. 6 shows the level of AR expression on the tested cancer cells. As expected, FACS analysis of AR expression in prostate and pancreatic cell lines are consistent with published expression levels: LNCaP>Panc1>PC3=MiaPaca2.

To better clarify the correlation between AR and IC$_{50}$, Table I was implemented with the addition of the AR expression levels of the tested cancer cell lines (Table II)

TABLE II

AR expression of Prostate & Pancreatic Cancer Cell Lines and IC$_{50}$ of Cortexolone-derived Compounds

| Cell Line Name | CB-03-01 C17 prop | CB-03-03 C17,21 but | CB-03-04 9dehy 17 but | CB-03-05 C17 val | CB-03-06 C17 ben | CB-03-10 C17,21 val | Enza lutamide | CPA | AR Expression |
|---|---|---|---|---|---|---|---|---|---|
| LNCaP | 33 | 16 | 46 | 32 | 12 | 10 | 38 | 22 | 9 |
| PC3 | 190 | 53 | 140 | 170 | 28 | 53 | 180 | 90 | 1 |

TABLE II-continued

AR expression of Prostate & Pancreatic Cancer Cell Lines and IC$_{50}$ of Cortexolone-derived Compounds

| Cell Line Name | CB-03-01 C17 prop | CB-03-03 C17,21 but | CB-03-04 9dehy 17 but | CB-03-05 C17 val | CB-03-06 C17 ben | CB-03-10 C17,21 val | Enza lutamide | CPA | AR Expression |
|---|---|---|---|---|---|---|---|---|---|
| Panc1 | 490 | 70 | 340 | 74 | 28 | 60 | 110 | 46 | 4 |
| MiaPaca2 | 110 | 30 | 160 | 59 | 20 | 37 | 65 | 39 | 1 |

As expected the growth inhibition shown by potent anti-androgens CPA and Enzalutamide correlates with the AR expression in prostate cancer cell lines. The inhibitory activities of CB-03-06 also correlate (less strictly) with AR expression in prostate cancer cells. However, there is an inverse correlation between AR expression and inhibitory activities in the pancreatic cancer cells. All tested compounds were more active in the lower AR expressing MiaPaca2 (AR$^{+/-}$) compared to the Panc1 cells (AR +). This result hints on a possible AR-independent mechanism of action in pancreatic cancer. CB-03-06 is the most potent compound in the series. Of note, CB-03-06 is better than CPA across all 4 cancer cell lines tested. CB-03-06 is also more potent than enzalutamide in prostate cancer cell lines.

Example 14: Analysis of In Vitro Anti-Cancer Activity of Cortexolone Derived Compounds in Particular CB-03-06 on a Larger Sample of Cancer Cell Lines Derived from Solid Tumors Since the cytotoxic activity of CB-03-06 appears to be independent from AR expression, a larger sample of solid tumors were tested. MCF7, a breast cancer cell line (AR+/−), an additional pancreatic cell line with higher AR expression (BxPC3) and intestinal cancer cell line (HT29) were added to the previous panel. Results are depicted in Table III.

CB-03-06 strongly inhibits cell viability of multiple cancer cell lines from different epithelial origin. The compound's cytotoxicity activity does not correlate with expression of androgen receptor. Nor does it correlate with the expression of wild type (WT). Additionally, CB-03-06 is more potent than Enzalutamide in all the cancer cell lines tested.

Example 15: Therapeutic Index of Cortexolone Derived Compounds on Different Cancer Cell Lines The therapeutic index (TI) (also referred to as therapeutic window, safety window, or therapeutic ratio) is a comparison of the amount of a therapeutic agent that causes the therapeutic effect to the amount that causes toxicity. IC$_{50}$ of the compounds was determined on fresh cells isolated from human blood (PBMC). The compound toxicity was determined as follow:

Therapeutic Index=Safety/Potency=IC$_{50}$ stimulated PBMC/IC$_{50}$ cancer cell

TABLE III

IC50 of Cortexolone-derived Compounds on cancer cell lines characterized by AR expression.

| | | in vitro proliferation IC50 (µM) | | | Genotype | |
|---|---|---|---|---|---|---|
| Tissue Type | Cell Line Name | CB-03-05 C17 val | CB-03-06 C17 ben | Enza lutamide | AR protein expression relative to PC3 | GR protein expression relative to LNCaP |
| Prostate Cancer | LNCaP | 32 | 12 | 38 | 9 | 1 |
| | PC3 | 170 | 28 | 180 | 1 | 2 |
| | 22Rv1 | | 25 | | pos based on literature | neg based on literature |
| Pancreatic Cancer | Panc1 | 74 | 28 | 110 | 4 | pos based on literature |
| | MiaPaca2 | 59 | 20 | 65 | 1 | 4 |
| | BxPC3 | | 28 | 127 | 3 | pos based on literature |
| Breast Cancer | MCF7 | 50 | 25 | 129 | 1 | 2 |
| | MDA-MB-231 | not active | 46 | 200 | 1 | 5 |
| Colon Cancer | HT29 | 35 | 13 | | pos based on literature | pos based on literature |
| Healthy Lymphocyte | PBMC RESTING | 120 | 85 | | nd | pos based on literature |
| | PBMC STIMULATED | 130 | 97 | 90 | nd | pos based on literature |

The results are shown in Table IV

TABLE IV

Therapeutic index of cortexolone derived compounds on a panel of cancer cell lines

| Type | Cell Line Name | CB-03-01 C17 prop | CB-03-03 C17, 21 but | CB-03-04 9dehy 17 but | CB-03-05 C17 val | CB-03-06 C17 ben | CB-03-10 C17, 21 val | Enzalutamide | CPA |
|---|---|---|---|---|---|---|---|---|---|
| *In vitro proliferation IC50 (micro Molar)* | | | | | | | | | |
| Prostate Cancer | LNCaP | 33 | 16 | 46 | 32 | 12 | 10 | 38 | 22 |
| | PC3 | 190 | 53 | 140 | 170 | 28 | 53 | 180 | 90 |
| Pancreatic Cancer | Panc1 | 490 | 70 | 340 | 74 | 28 | 60 | 110 | 46 |
| | MiaPaca2 | 110 | 30 | 160 | 59 | 20 | 37 | 65 | 39 |
| | BxPC3 | | | | | 28 | 30 | 127 | |
| Breast Cancer | MCF7 | 121 | 32 | 88 | 50 | 25 | 28 | 129 | 64 |
| Colon Cancer | HT29 | | | 51 | 35 | 16 | 34 | | |
| Healthy Lymphocyte | PBMC STIMULATED | 0.1 | 140 | 360 | 130 | 97 | 94 | 90 | 62 |
| *Therapeutic Index = IC50 resting PBMC/IC50 cancer cell* | | | | | | | | | |
| Prostate Cancer | LNCaP | 0 | 9 | 8 | 4 | 8 | 9 | 2 | 3 |
| | PC3 | 0 | 3 | 3 | 1 | 3 | 2 | 1 | 1 |
| Pancreatic Cancer | Panc1 | 0 | 2 | 1 | 2 | 3 | 2 | 1 | 1 |
| | MiaPaca2 | 0 | 5 | 2 | 2 | 5 | 3 | 1 | 2 |
| | BxPC3 | | | | | 3 | 3 | 1 | |
| Breast Cancer | MCF7 | 0 | 4 | 4 | 3 | 4 | 3 | 1 | 1 |
| Colon Cancer | HT29 | | | | 7 | 4 | 6 | 3 | |
| Healthy Lymphocyte | PBMC Stim | 1 | 1 | 1 | 1 | 1 | 1 | 1 | 1 |

All cortexolone derived compounds show a robust safety profile. CB-03-06 has the highest therapeutic index. This reveals that CB-03-06 has a safer profile compared to CPA and Enzalutamide.

Example 16—CB-03-06 Binding Affinity for the Androgen Receptor

The previous experiments demonstrated a strong cytotoxicity activity of CB-03-06 on cancer cell lines derived from tumors of different origins. This cytotoxic activity does not completely correlate with the anti-androgen receptor expression on the tested cancer cells.

Based on this evidence, assays to test the affinity of the compound to the androgen receptor (AR) were designed. To determine the relative binding affinities of CB-03-06 to the wild type AR, a competition assay using Polar Screen kit from Life Technologies was used. Briefly, the AR is added to a fluorescent androgen ligand (Fluormone™ AL Green) to form an AR-LBD complex. Competitors displace the fluorescent Fluormone™ AL Green ligand from the AR-LBD causing the fluorescent ligand to tumble rapidly during its fluorescence lifetime, resulting in a low polarization value. Non competitors will not displace the fluorescent ligand from the complex, so the polarization value remains high. The shift in polarization value in the presence of test compounds is used to determine relative affinity of test compounds for AR-LBD.

CB03-06 affinity for AR receptor was 2.6E-06 (IC50 molar). Within the same assay, the affinity of Dihydrotestosterone (a potent AR receptor binder) was 1.1E-08 CB-03-06 binding affinity for the AR receptor when compared to DHT is low and characterizes CB-03-06 as an AR potential binder.

Example 17—CB-03-06 Transcriptional Activity on the Glucocorticoid Receptor

The androgen and glucocorticoid hormones elicit divergent and often opposing effects in cells, tissues, and animals. A wide range of physiological and molecular biological evidence suggests that the receptors that mediate these effects, the androgen and glucocorticoid receptors (AR and GR, respectively), influence each other's transcriptional activity. CB-03-06 GR antagonist and agonist activities were tested on an in vitro assay. Briefly, human kidney epithelial cells were transfected with DNA construct containing GR binding sites linked to luminescent based reporter molecule. After 24 hours, cells were treated under antagonist or agonist modes. After an additional 24 hours, luminescence which is proportional to GR agonist transcriptional activity was quantitated.

Antagonist Assay was based on inhibition of luminescence induced by Dexamethasone (Dex).

Figure 7:
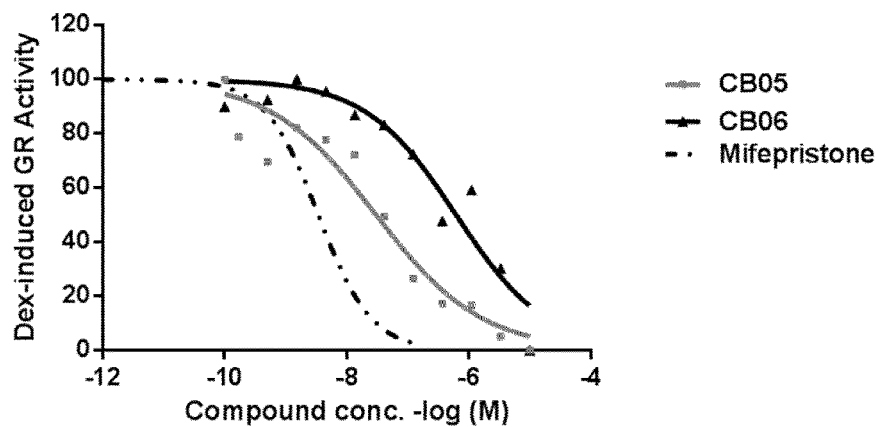
FIG. 7: CB-03-06 glucocorticoid antagonist activity.

The antagonist activity of CB-03-06 was compared to a known GR antagonist, Mifepristone (also called RU486) as shown in FIG. 7.

Agonist Assay—was based on induction of luminescence by CB-03-06

Figure 8:
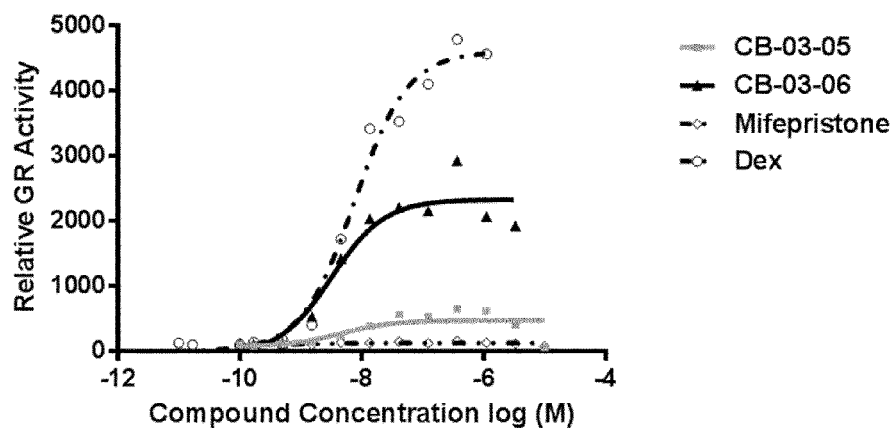
FIG. 8: CB-03-06 glucocorticoid agonist activity.

The agonist activity of CB-03-06 was compared to a RU486 which is known to not have agonist activity. As shown in FIG. 8.

As shown in FIG. 7, CB-03-06 is not a very potent antagonist (100 times less than RU486). By contrast, CB-03-

06 is a potent GR agonist at the concentration of 1.4E-08 M activating the GR to the same extent as 4.6E-09 M Dex. CB-03-06 is not as potent as Dex since its activity plateaus at 45% of Dex maximum. In conclusion, CB-03-06 is a weak GR antagonist and a good GR agonist.

Example 18—CB-03-06 Induction of Apoptosis and Cell Cycle Arrest

Most of the cytotoxic anticancer drugs in current use have been shown to induce apoptosis in susceptible cells. The fact that disparate agents, which interact with different targets, induce cell death with some common features suggests that cytotoxicity is determined by the ability of the cell to engage this so-called 'programmed' cell death. CB-03-06 was evaluated to determine if the mechanism of cytotoxicity on cancer cell lines was mediated by apoptosis and cell cycle arrest. Cancer cell lines were seeded in 6-well flat bottom plates. After 24 hours, test compounds or DMSO vehicle (negative control) were added. After an additional 24 hours, cells were scraped and stained with fluorescein conjugated Annexin V and propidium iodide, and analyzed by flow cytometry.

Figure 9:
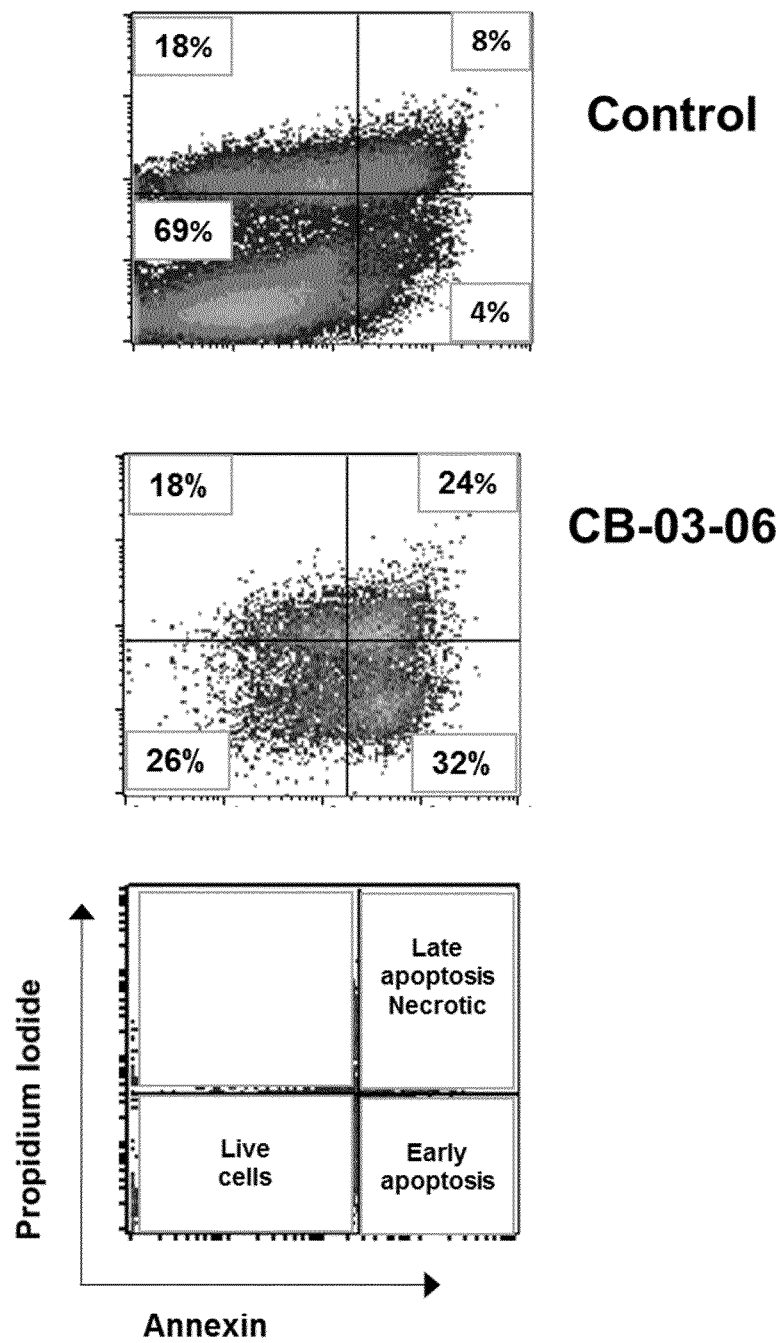
FIG. 9: CB-03-06 induction of apoptosis in MiaPaca2 cells.

FIG. 9 shows clearly how CB-03-06 is able to induce apoptosis in pancreatic cancer cell line MiaPaca2. CB-03-06 induces apoptosis in a total of 56% cells (early and late apoptosis) vs only 12% by the control.

Figure 10:
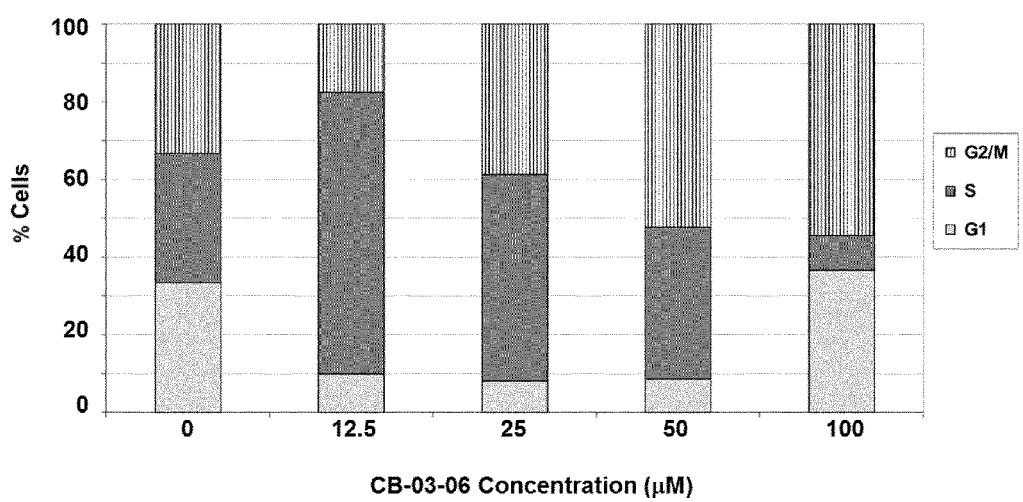
FIG. 10: Induction of cell cycle arrest by different concentrations of CB-03-06 in MiaPaca2 cells.

Apoptosis can occur at the G1/S or G2/M transition of the cell cycle. Cells were treated with CB-03-10 for 24 hours then fixed with paraformaldehyde and stained with propidium iodide. Data in FIG. 10 indicates CB-03-06 induces an S phase block at lower concentrations then a G2/M block at higher concentration. The lack of G1 block indicates no effect on p53. The S & G2/M blocks may indicate activity on cell cycle check point molecules. For S phase, a possible target is the cyclin dependent kinase 2 (CDK2). Gemzar and cisplatin are example drugs that act in S phase. For G2, a possible target is CDK1.

Example 19—Analysis of Caspase Induction by CB-03-06

From previous studies, it was determined that CB-03-06 induces apoptosis using Annexin V staining in MiaPaca2 cells. To better analyze the phenomenon, the enzymatic activity of Caspase 8 (initiator caspase for Extrinsic Pathway) and Caspase 9 (initiator caspase for Intrinsic Pathway) and of Caspases 3 and 7 (effector caspases) were measured.

Figure 11:
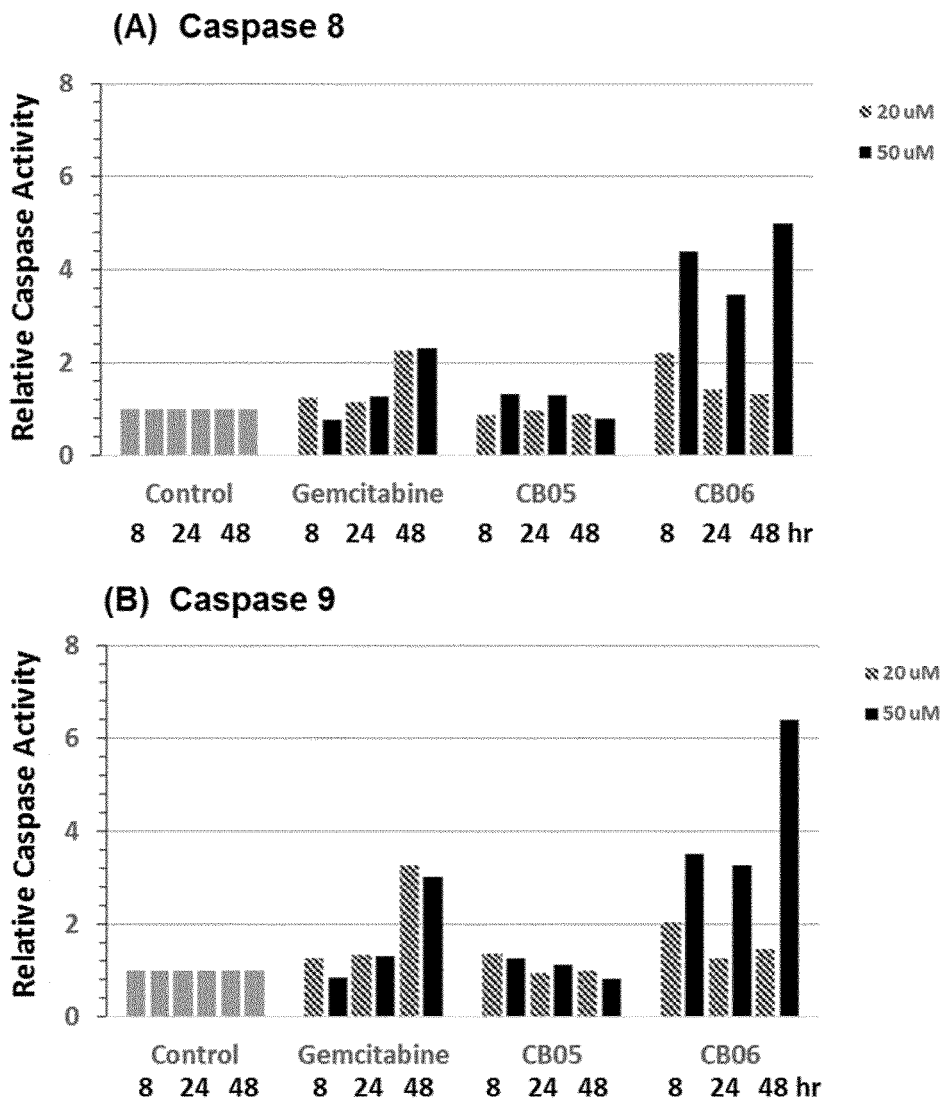
FIG. 11; Time course of caspases activation in MiaPaca2 Cells (8-24-48 hours). 20 μM (striped bars) or 50 μM (solid bars) indicate the compound's concentrations.
Figure 11:
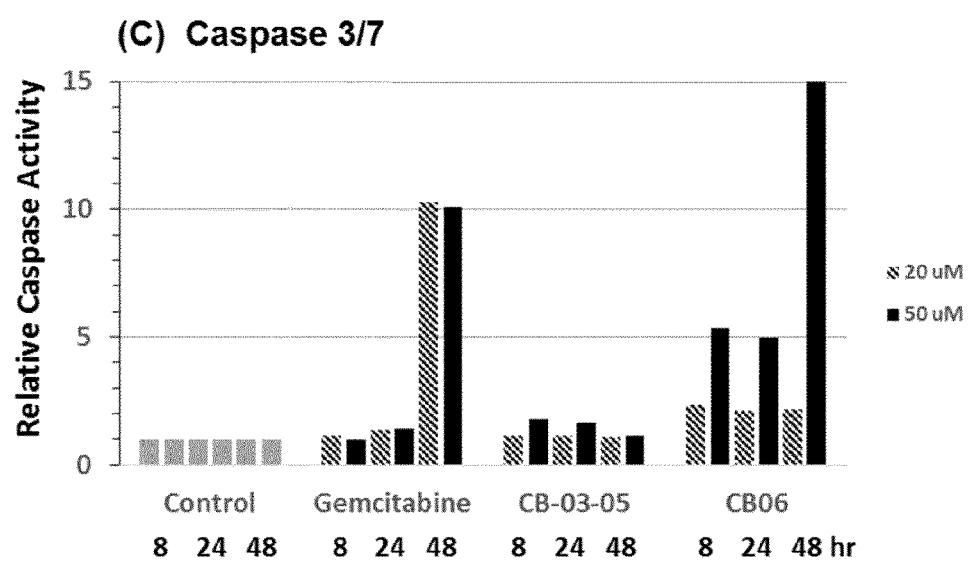

For this purpose, MiaPaca2 cells were seeded in 96 well flat bottom culture plates. After 24 hours, test compounds were added to cells. Gemcitabine (a known pancreatic cancer chemotherapeutic agent) and DMSO were used as positive and negative controls, respectively. There were three incubation time points: 8 hours, 24 hours, and 48 hours. After each time point, cells were lysed in multiplex buffer containing the caspase 3/7 substrate combined with either caspase 8 or caspase 9 reagents, which contain stable luciferase in proprietary buffers. The lysates were transferred to white opaque 96-well plates before measuring luminescence on a Tecan Safire instrument. Parallel plates treated identically were used to determine cell viability. All caspase activities were corrected for the number of viable cells. Results are shown in FIG. 11.

The activities of caspases 8 and 9 (panels A and B) were induced by CB-03-06. This induction was quick, dose-related, and already evident after 8 hours and was as high as 7-fold increase compared to the control.

Gemcitabine (a known chemotherapy agent used for pancreatic cancer treatment) also induced caspase 8 and 9 activities but with a delayed and less potent response compared to CB-03-06. The 2, 3-fold increase in Caspase 8 and 9 activity is not seen until the 48 hours mark.

Caspase 3/7 (panel C) were induced by CB-03-06 at high level after 48 hour incubation. Interestingly CB-03-05 does not show a good profile for caspase activation The same assay was repeated using LNCaP prostate cancer cell lines. For this assay, the positive control is Enzalutamide, a potent and novel anti antiandrogen currently used in clinical to treat prostate cancer patients. The results are shown in FIG. 12 after 24 hour incubation when the caspase activities peaked.

Figure 12:
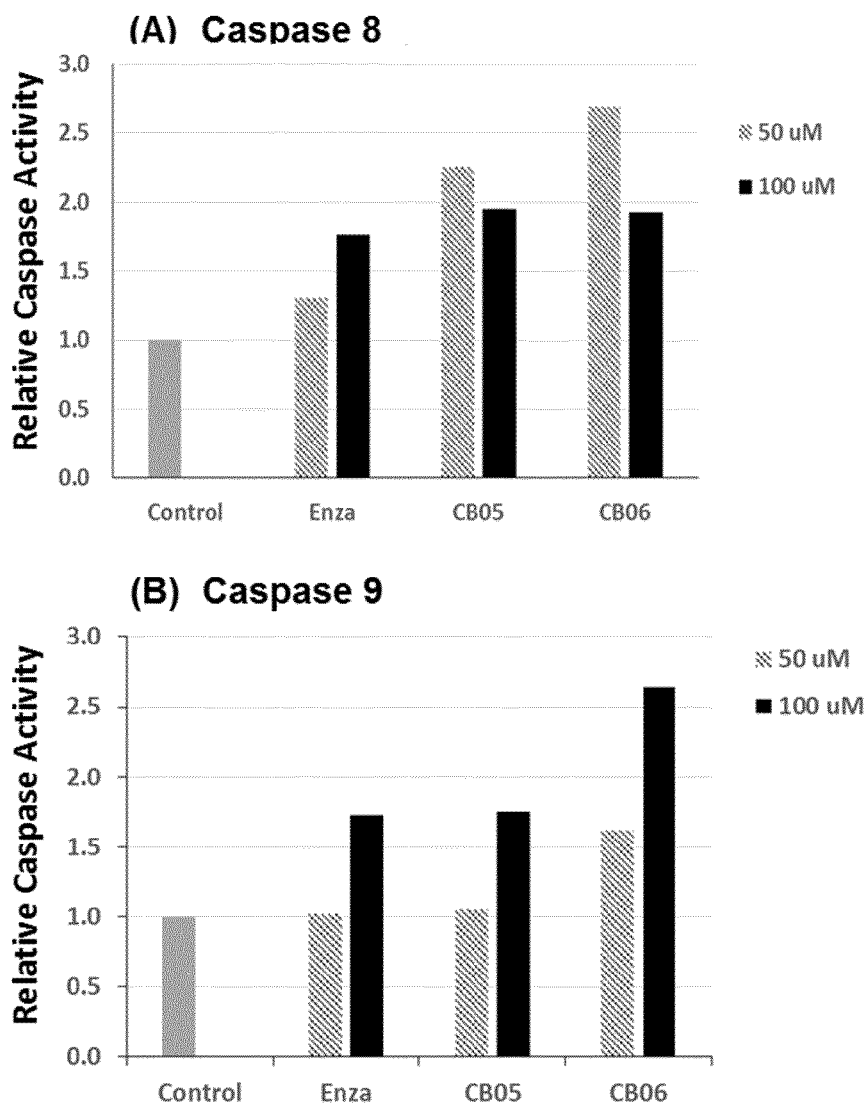
FIG. 12: Time course of caspase activation on LNCaP prostate cancer cell lines.
Figure 12:
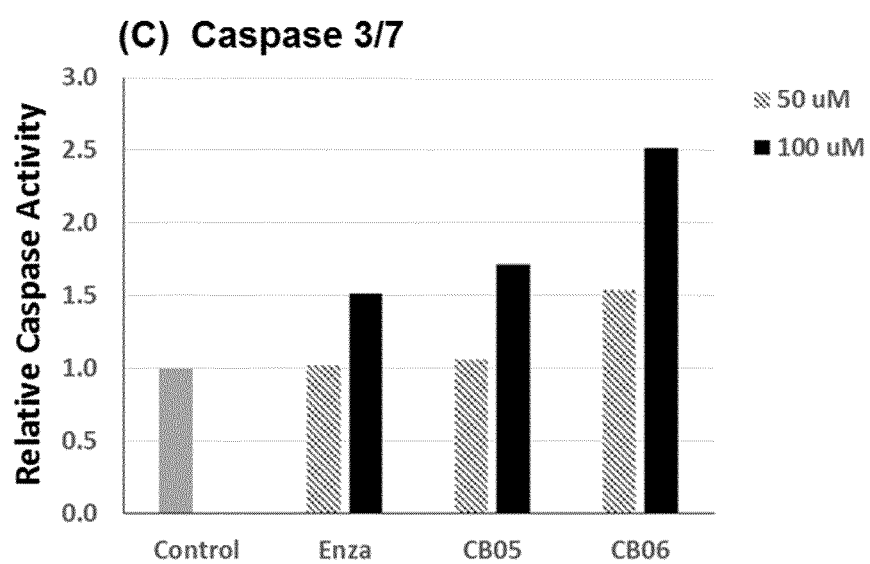

FIG. 12 clearly shows that CB-03-06 induced Initiator (8 and 9,) and Effector (3/7) caspase activities better than Enzalutamide (positive control).

These results showed CB-03-06 strong induction of caspases activity on prostate cancer cell lines, affecting both intrinsic and extrinsic pathways, confirming the inhibition observed on MiaPaca2 cell lines.

Example 20—CB-03-06 In Vitro Metabolism in Rat and Human Plasma

Figure 13:
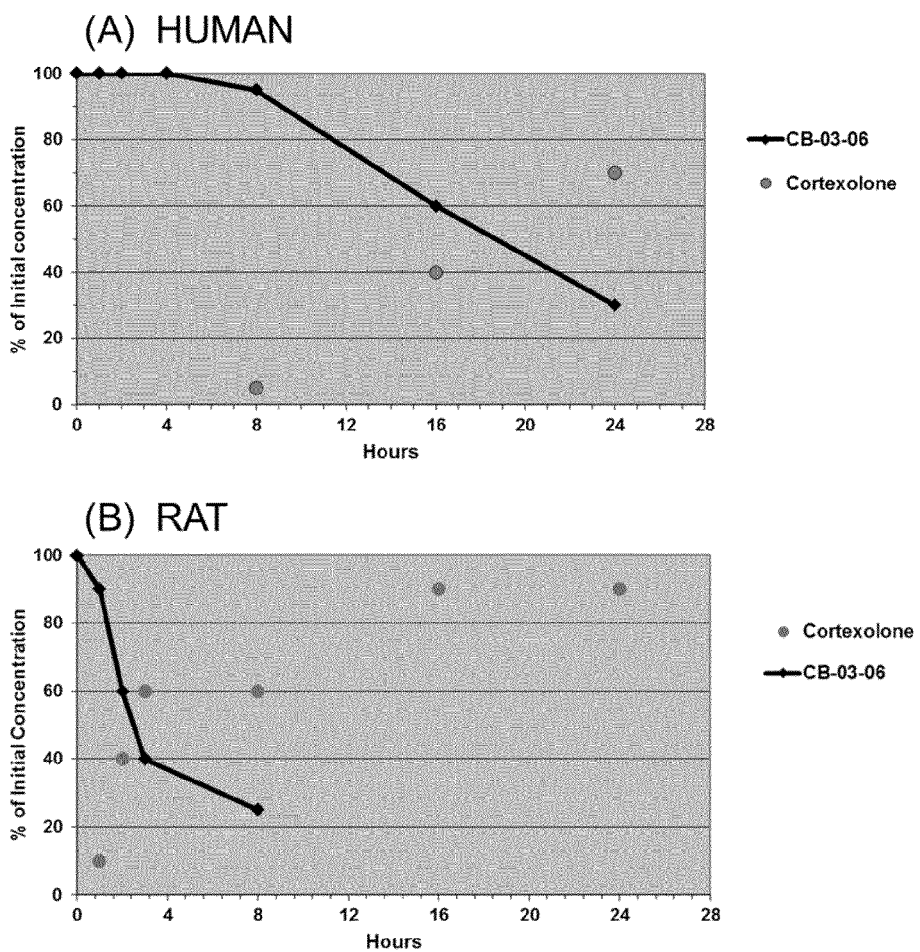
FIG. 13: In vitro metabolism of CB-03-06 in (A) Human and (B) Rat plasma.
Figure 14:
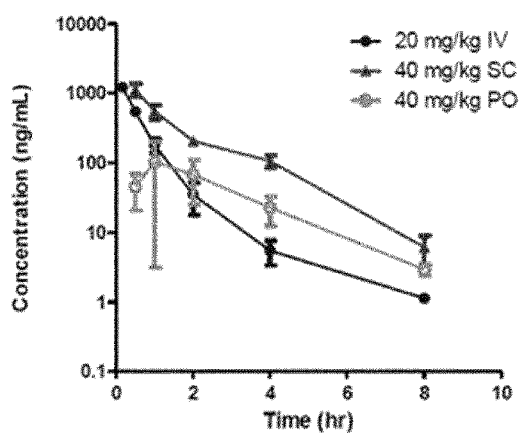
FIG. 14: CB-03-06 pharmacokinetics evaluated in vivo in plasma of mice after subcutaneous and oral administration.

To obtain some insight on the metabolism of CB-03-06 in human and rat plasma, a specific assay was designed. Briefly, the compound was incubated at different time points in human and rat plasma at 37 C. After incubation, the samples were tested for presence of the intact compound by liquid chromatography. The time course and concentration are shown in FIG. 13.

The results show CB-03-06 maintains over 90% of initial concentration through 8 hours in plasma and degrades faster in rat compared to human plasma.

Example 21—Analysis of CB-03-06 In Vivo Pharmacokinetic in an Animal Model (Mouse)

The pharmacokinetic of CB-03-06 was evaluated in plasma of mice after intravenous (iv), subcutaneous (SC) and oral administration (PO).

Mice (3 per group) were administered with the following doses and blood was collected at the indicated times. Plasma samples were analyzed by HPLC-MS/MS.

| Group | Dosing Route | Blood Collection Time Point |
| --- | --- | --- |
| 1 | iv (20 mg/kg) | 10 min, 1 hr, 4 hr |
| | | 30 min, 2 hr, 8 hr |
| 2 | SC (40 mg/kg) | 30 min, 2 hr, 8 hr |
| | | 1 hr, 4 hr, 24 hr |
| 3 | PO (40 mg/kg) | 30 min, 2 hr, 8 hr |
| | | 1 hr, 4 hr, 24 hr |

The actual body exposure to CB-03-06 (as reflected by the AUC) is highest after subcutaneous administration (1620 hour*ng/mL), down to 50% when given intravenously (896), and to 17% when given orally (276).

Example 22—In Vivo Testing of CB-03-06 in a Mouse Xenograft Model of Human Pancreatic Cancer (MiaPaca2 Cell Line)

Figure 15:
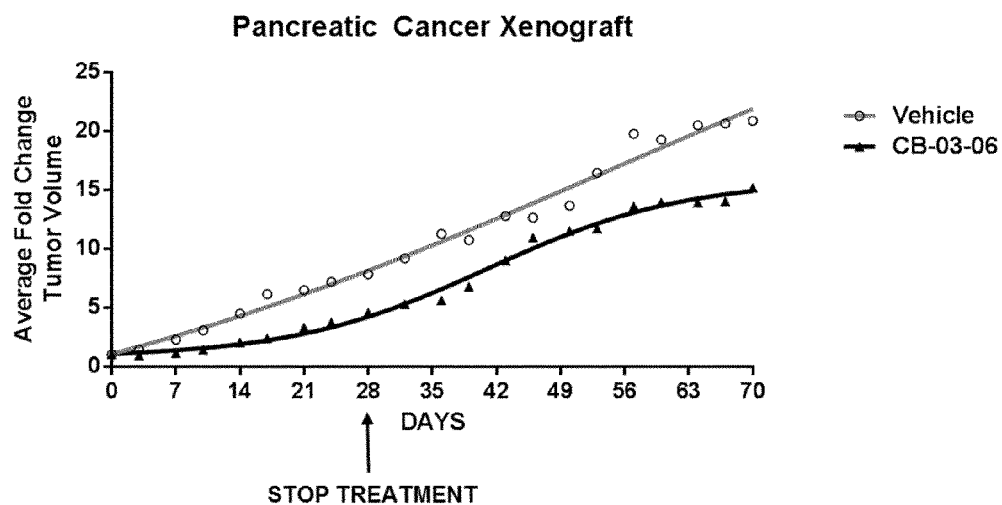
FIG. 15: CB-03-06 in vivo anti-tumor activity on mouse xenograft model of pancreatic cancer when administered subcutaneosly.

From previous studies CB-03-06 was observed to strongly inhibit the in vitro growth of MiaPaca2 pancreatic cells lines ($AR^{+/-}$). An investigation to whether this result could be translated into an in vivo xenograft pancreatic cancer model was performed. Cyproterone acetate (CPA), a well-known anti-androgen, was used as control. Briefly $1 \times 10^6$ MiaPaca2 cells suspended in matrigel were subcutaneously (sc) injected into 6 week old male athymic nude mice. Tumors were measured every 4 days with a digital caliper. Tumor volume was calculated according to the formula: $0.5236(r1)2(r2)$ where $r1<r2$. Treatment with CB-03-06 and control compounds were initiated after the tumor had reached 50 mm$^3$. Compounds diluted in DMSO/ 2-hydroxypropyl b-cyclodextrin (vehicle) were subcutaneously injected daily (100 microL/mouse) at the concentration of 40 mg/Kg daily for 28 consecutive days. FIG. 15 shows the average tumor increase in the in vivo xenograft model after sc injection of CB-03-06 when compared to the vehicle In FIG. 15, CB-03-06 shows a significant in vivo anti-pancreatic tumor activity when compared to the controls. It also shows a significant anti-tumor activity ($p<0.5$) when compared to vehicle only or CPA (not shown).

During the treatment period CB-03-06 maintained the pancreatic tumor size to less than 5-fold relative to the initial size. In contrast, the average tumor in the vehicle or CPA treatment groups increased in size to 12-fold. Not only does CB-03-06 show to inhibit the tumor growth, it also shows a benefit in the mice survival. Median survival was 70 days for mice treated with CB-03-06 compared to 60 days for vehicle treated mice or 40 days with CPA. This difference is significant with a 2 to 4 time higher risk of death in the vehicle treated group.

Example 23—In Vivo Testing of CB-03-06 Administered Orally in a Mouse Xenograft Human Prostate Cancer Model (LNCaP Cells)

Figure 16:
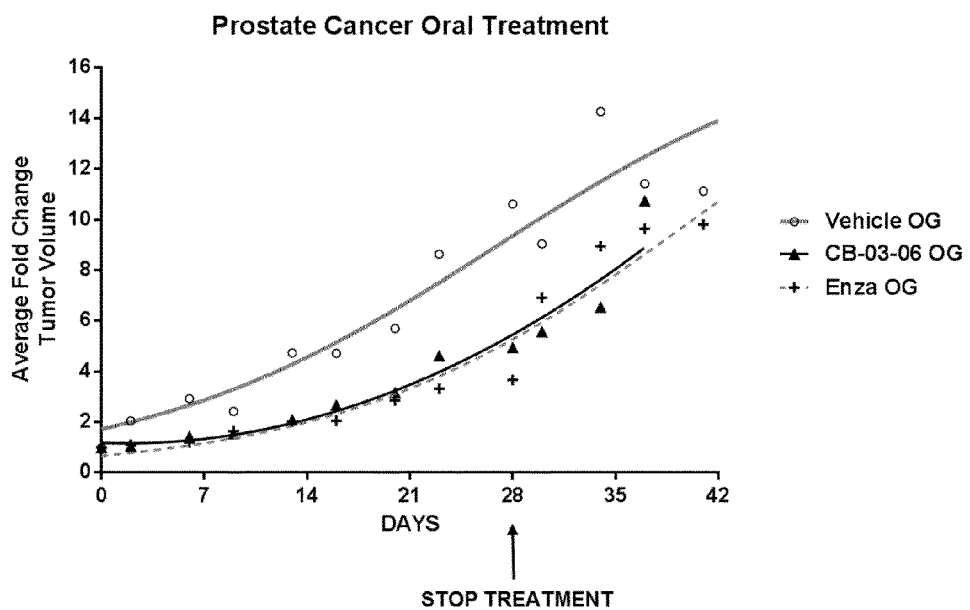
FIG. 16: CB-03-06 in vivo anti-tumor activity in a mouse xenograft model of prostate cancer when administered by oral gavage.
Figure 17:
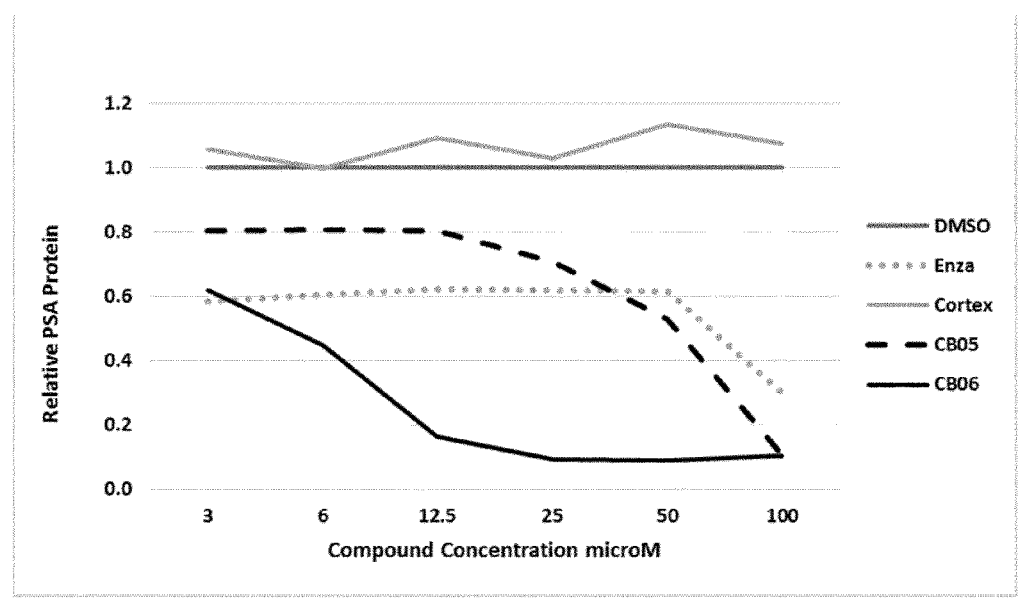
FIG. 17; CB-03-06 Inhibition of in vitro baseline PSA secretion from LNCaP cancer cell lines.

From previous studies CB-03-06 was observed to be also effective in inhibiting in vitro the growth of LNCaP prostate cancer cells lines. An investigation to whether this result could be translated into an in vivo xenograft prostate cancer model was performed. $3 \times 10^6$ LNCaP cells suspended in matrigel were subcutaneously injected (on the right flank) into 6 week old male athymic nude mice. Tumors were measured as described above. Treatment with CB-03-06 and controls compounds was initiated after the tumor had reached 50 mm$^3$. Formulations for dosing were prepared in 15% Vitamin E-TPGS and 65% of a 0.5% w/v CMC solution in 20 mM citrate buffer (pH 4). Oral dosing was daily (100 mg/Kg in 200 microL/mouse) for 28 consecutive days. Results were plotted as average change in tumor volume relative to the start of treatment. FIG. 16 shows the results obtained from the in vivo xenograft prostate cancer model after oral administration of CB-03-06. Enzalutamide is a novel and potent anti-androgen, and serves as a positive control.

The trend for the oral dosed CB-03-06 shows a strong anti-tumor activity against prostate cancer. The inhibitory activity is almost identical to that of Enzalutamide, which is the current medication used treatment of androgen-dependent prostate cancer in human.

Example 24—CB-03-06 Inhibition of In Vitro Prostate-Specific Antigen (PSA) Secretion from LNCaP Prostate Cancer Cells Prostate-specific antigen, or PSA, is a protein produced by cells of the prostate gland. The PSA test measures the level of PSA in a man's blood. The blood level of PSA is often elevated in men with prostate cancer and it used as surrogate marker to test prostate cancer progression in human population. After the observation that CB-03-06 was able to inhibit in vivo the growth of prostate cancer, the capability of the compound to inhibit in vitro PSA secretion from cancer cell was determined. LNCaP cells were seeded in 96-well flat bottom culture plates in media containing charcoal stripped serum with or without 10 nM DHT. After 24 hours, test compounds are added to cells, using DMSO as the vehicle negative control and Enzalutamide as the positive control. After 48 hours incubation with test compounds, supernatants were harvested and tested with an Elisa assay for PSA and the same cells were lysed for cell viability assessment.

As expected the pure anti-androgen, Enzalutamide, is potent at inhibiting PSA secretion with an IC50.<3 µM. CB-03-06 is also a potent PSA inhibitor (IC50 4 µM). However, Enzalutamide activity did not titrate as well as CB-03-06. Of note, Cortexolone, the parent and final metabolite of all our compounds, is essentially inactive on PSA secretion (IC50 612 µM). When cell viability of these cells was tested, Enzalutamide had an IC50 of 61 µM and CB-03-06 showed an IC50 of 12. This confirms the strong growth inhibitory activity of both compounds. Importantly, Cortexolone inhibits LNCaP viability only at very high concentration (IC50 153 µM) and can be define as inactive as cytotoxic compound for cancer cell lines.

Example 25—Analysis of In Vitro Anti-Cancer Activity of CB-03-06 on Breast Cancer Cell Lines Triple Negative Breast Cancer (TNBC) accounts for around 20% of newly diagnosed invasive breast cancer. This cancer is not supported by hormones estrogen and progesterone, nor by the presence of too many HER2 receptors, for this reason patients do not respond to conventional therapy (eg tamoxifen or Herceptin). Consequently, TNBC is characterized to be resistant to chemotherapy and has low survival.

There is a correlation between this cancer resistance and high GR expression (Cancer therapy 2013). There are clinical trials testing a GR antagonist (Mifepristone/RU486) in combination with chemotherapy for the treatment of TNBC. However, mifepristone clinical use is compromised due to poly pharmacology tied to progesterone receptor (PR) antagonism. To evaluate if CB-03-06 can be used as potential treatment for breast cancer, and in particular TNBC, a cytotoxic assays was performed using breast cancer cell lines characterized by various hormone receptor expression The breast cancer cell lines selected were:

MCF7 breast cancer cells (ER$_+$PR$_+$Her2$_+$, GR$_{+/-}$)

MDA-MB-231 TBNC cells (ER_PR_Her2_, GR$_{++}$)

Figure 18:
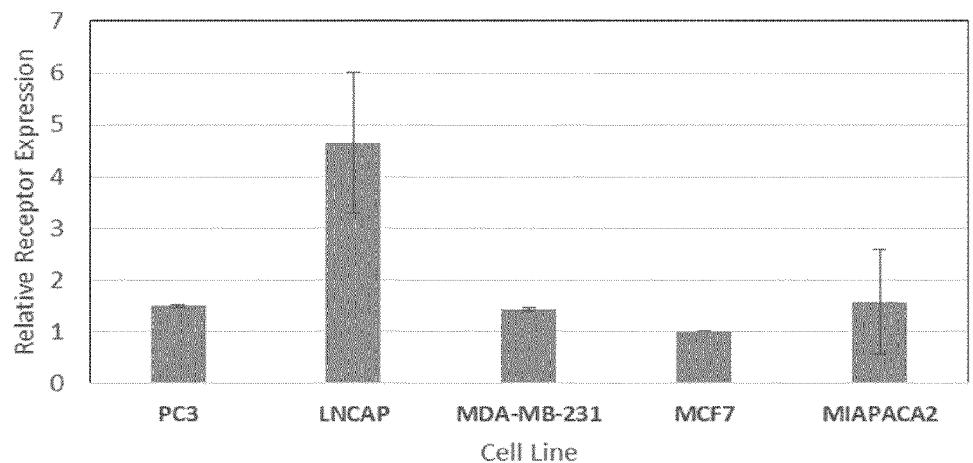
FIG. 18: Androgen and Glucorticoid receptor expression in different cancer cell lines.
Figure 18:
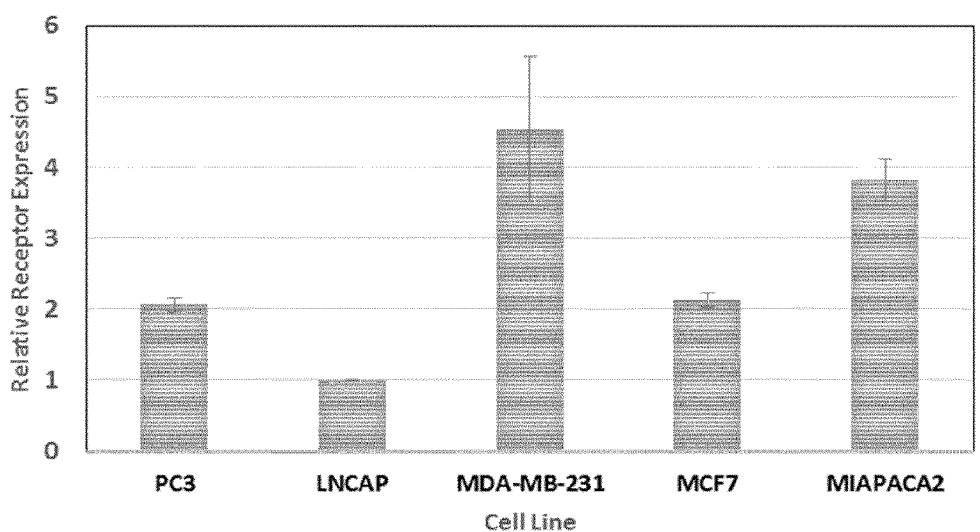

Before testing cell growth inhibition, breast cancer cells were characterized for AR and GR receptor expression by FACS as previously described. The data in FIG. 18 confirm the receptor expression as indicated in the literature.

For the cytotoxic assay, cells were seeded in 96-well flat bottom culture plates in media containing charcoal stripped serum. After 24 hours, test compounds were added to the cells. DMSO was used as the vehicle negative control and RU486 as the positive control. After 72 hour incubation, cells were harvested and lysed to determine cell viability using the Cell Titer Glow assay.

Table VI shows the IC50 of CB-03-06 on the above mentioned breast cancer cells lines.

|  | MCF7 (ER$^+$PR$^+$GR$^{+/-}$) | MDA-MB-231 (ER$^-$PR$^-$GR$^{++}$) |
|---|---|---|
| RU486 | Not active | 435 |
| CB-03-06 | 25 | 46 |

CB-03-06 is active on both breast cancer cell lines, but it seems more active in MCF7 cells than MDA-MB-231, perhaps hinting that GR is not the only target of this compound. RU486, mifepristone, (GR/PR antagonist) does not affect, as expected, viability of GR$^{+/-}$ MCF7 cells, while inhibits, at a very low extent, the viability of TNBC GR$^+$ MDA-MB-231 cells to a maximum of 25% at 100 μM.

Interestingly, CB-03-05 is only active in MCF7, not in MDA-MB-231. It is not clear which receptor is responsible for this differential effect because these cells are different for at least 4 receptors. If not GR, then could be ER (Estrogen Receptor) (ER), PR (Progesterone Receptor) or Her2 which are expressed in MCF7 but not MDA MDA-MB-231.

GENERAL CONCLUSION

These examples demonstrate that cortexolone 17α-benzoate (CB-03-06), in particular, has superior activity beyond other known cortexolone derived compounds. We have observed improved results both in-vitro and in-vivo in terms of, for example
I) general in-vitro anti-tumoral activity;
II) in-vitro anti-tumoral activity not directly correlated to AR expression;
III) II) in-vitro anti-tumoral activity directly correlated to GR expression;
IV) therapeutic index (TI); and
V) In vivo anti-tumoral activity against pancreatic and prostate tumors.

I) It is clear from the data shown in Table I that cortexolone derived compounds kill cancer cells at various concentration and IC$_{50}$. However, CB-03-06 and CB-03-10 show the best IC$_{50}$ when compared to the other compounds in the cortexolone derived series across cancer cell lines of different origin. Even the metabolite CB-03-05 of CB-03-10, show good IC50 value in LNCaP prostate cancer cells (IC50 32 microM). The lower IC$_{50}$ depose for a stronger in vitro anti tumoral activity.

I) It is clear from the data shown in Table I that cortexolone derived compounds kill cancer cells at various concentration and IC$_{50}$. However, CB-03-06 and CB-03-10 show the best IC$_{50}$ when compared to the other compounds in the cortexolone derived series across cancer cell lines of different origin. Even the metabolite CB-03-05 of CB-03-10, show good IC50 value in LNCaP prostate cancer cells (IC50 32 microM).

The lower IC$_{50}$ depose for a stronger in vitro anti tumoral activity.

TABLE I

| | IC$_{50}$ of Cortexolone-derived Compounds tested in Prostate & Pancreatic Cancer Cell Lines | | | | | | | |
|---|---|---|---|---|---|---|---|---|
| Cell Line Name | CB-03-01 C17 prop | CB-03-03 C17, 21 but | CB-03-04 9dehy 17 but | CB-03-05 C17 val | CB-03-06 C17 ben | CB-03-10 C17, 21 val | Enza lutamide | CPA |
| LNCaP | 33 | 16 | 46 | 32 | 12 | 10 | 38 | 22 |
| PC3 | 190 | 53 | 140 | 170 | 28 | 53 | 180 | 90 |
| Panc1 | 490 | 70 | 340 | 74 | 28 | 60 | 110 | 46 |
| MiaPaca2 | 110 | 30 | 160 | 59 | 20 | 37 | 65 | 39 |

II) The androgen receptor (AR) expression was tested on the cancer cell lines, see Table II As expected the growth inhibition shown by potent anti-androgens CPA and Enzalutamide correlates with the AR expression in prostate cancer cells. Notably the activity of CB-03-06 and CB-03-10 is independent from the androgen receptor. CB-03-04 shows an IC$_{50}$ of 46 when tested on LNCaP (prostate cancer cell line that express androgen receptor) but an IC$_{50}$ much higher (135) when tested on PC3 that express low or null Androgen receptors. CB-03-06 and CB-03-10 shown a very good IC$_{50}$ almost irrespective of the AR expression. The same behavior was observed on pancreatic cell lines.

TABLE II

| | AR expression of Prostate & Pancreatic Cancer Cell Lines and IC$_{50}$ of Cortexolone-derived Compounds | | | | | | | | |
|---|---|---|---|---|---|---|---|---|---|
| Cell Line Name | CB-03-01 C17 prop | CB-03-03 C17, 21 but | CB-03-04 9dehy 17 but | CB-03-05 C17 val | CB-03-06 C17 ben | CB-03-10 C17, 21 val | Enza lutamide | CPA | AR Expression |
| LNCaP | 33 | 16 | 46 | 32 | 12 | 10 | 38 | 22 | 9 |
| PC3 | 190 | 53 | 140 | 170 | 28 | 53 | 180 | 90 | 1 |
| Panc1 | 490 | 70 | 340 | 74 | 28 | 60 | 110 | 46 | 4 |
| MiaPaca2 | 110 | 30 | 160 | 59 | 20 | 37 | 65 | 39 | 1 |

III) The therapeutic index (TI) (also referred to as therapeutic window, safety window, or therapeutic ratio) is a comparison of the amount of a therapeutic agent that causes the therapeutic effect to the amount that causes toxicity. $IC_{50}$ of the compounds was determined on fresh cells isolated from human blood (PBMC). The compound toxicity was determined as follow:

Therapeutic Index=Safety/Potency=$IC_{50}$ stimulated PBMC/$IC_{50}$ cancer cell The results are shown in Table VII. All cortexolone derived compounds show a robust safe toxicity profile. However CB-03-06 showed the highest therapeutic index when tested across all 7 cancer cell lines tested in vitro.

TABLE VII

| | | Therapeutic Index = IC50 stimulated PBMC/IC50 cancer cell | | | | | | | |
|---|---|---|---|---|---|---|---|---|---|
| Tissue Type | Cell Line Name | CB-03-01 C17 prop | CB-03-03 C17, 21 but | CB-03-04 9dehy 17 but | CB-03-05 C17 val | CB-03-06 C17 ben | CB-03-10 C17, 21 val | Enza lutamide | CPA |
| Prostate Cancer | LNCaP | 0 | 9 | 8 | 4 | 8 | 9 | 2 | 3 |
| | PC3 | 0 | 3 | 3 | 1 | 3 | 2 | 1 | 1 |
| Pancreatic Cancer | Panc1 | 0 | 2 | 1 | 2 | 3 | 2 | 1 | 1 |
| | MiaPaca2 | 0 | 5 | 2 | 2 | 5 | 3 | 1 | 2 |
| | BxPC3 | | | | | 3 | 3 | 1 | |
| Breast Cancer | MCF7 | 0 | 4 | 4 | 3 | 4 | 3 | 1 | 1 |
| Colon Cancer | HT29 | | | 7 | 4 | 6 | 3 | | |
| AVERAGE | | 0 | 4 | 4 | 3 | 5 | 4 | 1 | 1 |

Therapeutic index of cortexolone derived compounds on a panel of cancer cell lines IV) Triple negative breast cancer (TNBC) as shown in example 24. The cytotoxic activity shown by CB-03-06 is particularly impressive because usually conventional therapeutic agents do not work on triple negative breast cancer (TNBC) cell lines. TNBC is defined as the absence of estrogen and progesterone receptor expression as well as ERBB2 amplification. It has no response to endocrine or anti-ERBB2 therapies. Recent studies have found some potential therapeutic targets for TNBC. However, it still has a poor outcome. Taking into consideration the cytotoxic activity and the excellent safety profile of CB-03-06; CB-03-06 is a new and improved candidate for the clinical treatment of this cancer.

The invention will now be described by the following numbered embodiments.

1. In one embodiment the invention is a compound of formula (I)

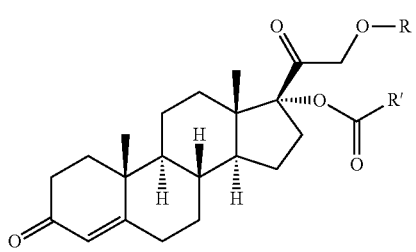

(I)

wherein R is hydrogen or C(O)—$R_1$, wherein $R_1$ is a linear alkyl chain containing 2 to 5 carbon atoms, and wherein R' is a linear alkyl chain containing 3 to 6 carbon atoms or an optionally substituted aryl group or an optionally substituted heteroaryl group.

2. In another embodiment the invention is a compound of formula (I) according to statement 1 wherein the optionally substituted aryl group is phenyl.

3. In another embodiment the invention is a compound of formula (I) according to statement 1 wherein $R_1$ is hydrogen or $CH_2CH_3$, and R' is —$(CH_2)_3$—$CH_3$ or phenyl.

4. In another embodiment the invention is a compound according to statement 1 having formula:

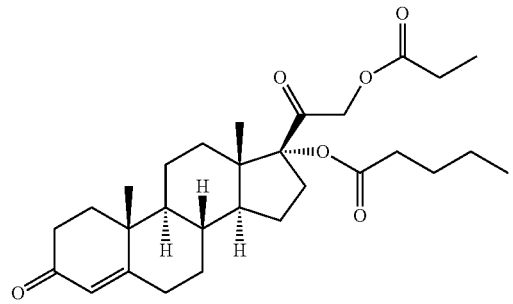

5. In another embodiment the invention is a compound according to statement 1 having formula:

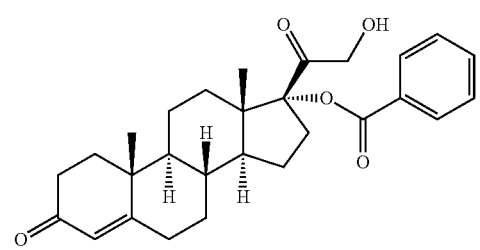

6. In another embodiment the invention is a compound according to any of statements 1 to 5 for use as a medicament.

7. In another embodiment the invention is a compound according to any of statements 1 to 5 for use in the treatment of precancerous lesions, dysplasias, metaplasias and tumor diseases.

8. In another embodiment the invention is a compound for use according to statement 7, characterized in that said tumor disease includes malignant neoplasias and metastasis.

9. In another embodiment the invention is a compound for use according to statement 8, characterized in that said tumor diseases are solid tumors, preferably epithelial tumors, such as prostate carcinoma; mammary carcinoma; pancreatic carcinoma; lung carcinoma; gastrointestinal tract carcinoma, such as colon carcinoma; kidney cancer; thyroid carcinoma; uterine carcinoma; adrenal carcinoma.

10. In another embodiment the invention is a compound for use according to statement 9, characterized in that said epithelial tumors are prostate carcinoma or pancreatic carcinoma, preferably exocrine pancreatic carcinoma.

11. In another embodiment the invention is a pharmaceutical composition comprising at least one compound of formula (I) according to any of statements 1 to 5, in association with at least one physiologically acceptable excipient.

12. In another embodiment the invention is pharmaceutical compositions according to statement 11, characterized in that they are in solid or in liquid form.

13. In another embodiment the invention is pharmaceutical compositions in solid form according to statement 12, characterized by being powders, freeze-dried powders, granules, pellets, tablets or capsules.

14. In another embodiment the invention is pharmaceutical compositions in liquid form according to statement 12, characterized by being solutions, emulsions, suspensions or syrups.

15. In another embodiment the invention is a pharmaceutical composition according to any of statements 11 to 14, characterized by containing at least another active ingredient, preferably a chemotherapeutic active ingredient, as a combination for simultaneous, separate or sequential administration.

16. In another embodiment the invention is a pharmaceutical composition according to statements 11 to 15 for use in the treatment of precancerous lesions, dysplasias, metaplasias and tumor diseases.

17. In another embodiment the invention is a pharmaceutical composition for use according to statement 16, characterized in that said tumor diseases include malignant neoplasias and metastasis.

18. In another embodiment the invention is a pharmaceutical composition for use according to statement 17, characterized in that said tumor diseases are solid tumors, preferably epithelial tumors, such as prostate carcinoma; mammary carcinoma; pancreatic carcinoma; lung carcinoma; gastrointestinal tract carcinoma, such as colon carcinoma; kidney cancer; thyroid carcinoma; uterine carcinoma; adrenal carcinoma.

19. In another embodiment the invention is a pharmaceutical composition for use according to statement 18, characterized in that said epithelial tumors are prostate carcinoma or pancreatic carcinoma, preferably exocrine pancreatic carcinoma.

The invention claimed is:

1. A method of treating a tumor disease in a subject in need thereof, comprising administrating to said subject a therapeutically effective amount of a compound having formula:

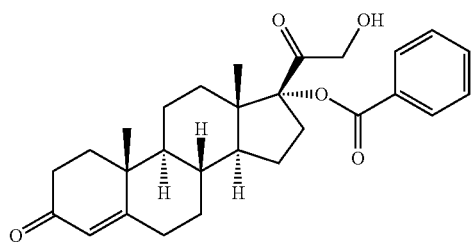

or a pharmaceutical composition comprising said compound; wherein the tumor disease is a solid epithelial tumor selected from prostate carcinoma, mammary carcinoma, pancreatic carcinoma, and colon carcinoma.

2. The method of claim 1, wherein the subject is a mammal.

3. The method of claim 2, wherein the mammal is a human.

4. The method according to claim 1, wherein the prostate carcinoma is or becomes resistant to anti-androgen targeted therapy.

5. The method according to claim 1, wherein the pancreatic carcinoma is exocrine pancreatic carcinoma.

6. The method of claim 1, wherein the mammary carcinoma is triple negative breast cancer.

7. The method of claim 6 wherein the subject is a relapsed or a non-responder to conventional therapy.

8. A method of treating a tumor in a subject in need thereof, the method comprising administrating to said subject a therapeutically effective amount of a compound having formula:

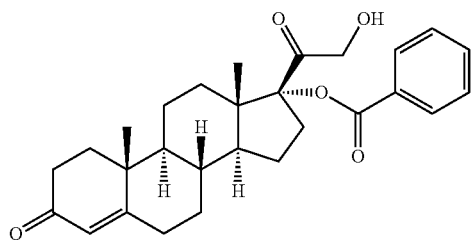

or a pharmaceutical composition comprising said compound; wherein the tumor is a solid epithelial tumor selected from prostate carcinoma, mammary carcinoma, pancreatic carcinoma, and colon carcinoma.

9. The method of claim 8, wherein the subject is a mammal.

10. The method of claim 9, wherein the mammal is a human.

11. The method according to claim 8, wherein the prostate carcinoma is or becomes resistant to anti-androgen targeted therapy.

12. The method according to claim 8, wherein the pancreatic carcinoma is exocrine pancreatic carcinoma.

13. The method of claim 8, wherein the mammary carcinoma is triple negative breast cancer.

14. The method of claim 13 wherein the subject is a relapsed or a non-responder to conventional therapy.

* * * * *